(12) United States Patent
Mitri et al.

(10) Patent No.: US 9,383,238 B2
(45) Date of Patent: Jul. 5, 2016

(54) APPARATUS, SYSTEM AND PROCESS FOR CHARACTERIZING MULTIPHASE FLUIDS IN A FLUID FLOW STREAM

(71) Applicants: Farid G. Mitri, Santa Fe, NM (US); Cole T. Brinkley, Peralta, NM (US); Robert Louis Williford, Los Alamos, NM (US)

(72) Inventors: Farid G. Mitri, Santa Fe, NM (US); Cole T. Brinkley, Peralta, NM (US); Robert Louis Williford, Los Alamos, NM (US)

(73) Assignee: CHEVRON U.S.A. INC., San Ramon, CA (US)

( * ) Notice: Subject to any disclaimer, the term of this patent is extended or adjusted under 35 U.S.C. 154(b) by 71 days.

(21) Appl. No.: 14/549,391

(22) Filed: Nov. 20, 2014

(65) Prior Publication Data

US 2015/0233747 A1    Aug. 20, 2015

Related U.S. Application Data

(60) Provisional application No. 61/941,694, filed on Feb. 19, 2014.

(51) Int. Cl.
  *G01F 1/66* (2006.01)
  *G01F 1/74* (2006.01)
  *G01N 29/024* (2006.01)

(52) U.S. Cl.
  CPC .. *G01F 1/66* (2013.01); *G01F 1/74* (2013.01); *G01N 29/024* (2013.01);
  (Continued)

(58) Field of Classification Search
  CPC ........................................................ G01F 1/66
  USPC ........................................ 73/861.28, 861.27
  See application file for complete search history.

(56) References Cited

U.S. PATENT DOCUMENTS

| 3,564,912 | A | * | 2/1971 | Malone et al. | G01F 1/668 73/861.31 |
| 4,024,760 | A | * | 5/1977 | Estrada, Jr. | G01P 5/245 73/861.31 |

(Continued)

FOREIGN PATENT DOCUMENTS

GB        2504295         1/2014

OTHER PUBLICATIONS

I. Ismail, J.C. Gamino, S.F.A. Bukhari and W.Q. Yang; Tomography for muti-phase flow measurement in the oil industry; Science Direct; Feb. 14, 2005; pp. 145-155.

(Continued)

*Primary Examiner* — Jewel V Thompson
(74) *Attorney, Agent, or Firm* — King & Spalding LLP

(57) ABSTRACT

A system for determining characteristics of a multiphase fluid includes pipe and multiple pairs of transducers positioned circumferentially around the pipe. Each pair of transducers includes a transmitting transducer and a receiving transducer. The transmitting transducer of each pair of transducers is oriented to transmit a respective acoustic signal toward the receiving transducer of the pair of transducers. The transmitting transducer of each pair of transducers is operable to transmit the respective acoustic signal sequentially with respect to other transmitting transducers of the multiple pairs of transducers. A reception of a first acoustic signal transmitted by a transmitting transducer of a first pair transducers of the multiple pairs of transducers is completed by a receiving transducer of the first pair transducers before a transmitting transducer of another pair transducers of the multiple pairs of transducers transmits a second acoustic signal.

20 Claims, 20 Drawing Sheets

(52) U.S. Cl.
CPC ... *G01N 2291/021* (2013.01); *G01N 2291/022* (2013.01); *G01N 2291/02809* (2013.01); *G01N 2291/105* (2013.01)

(56) References Cited

U.S. PATENT DOCUMENTS

| | | | |
|---|---|---|---|
| 4,032,259 A | 6/1977 | Brown | |
| 6,089,104 A | 7/2000 | Chang | |
| 6,354,146 B1 | 3/2002 | Birchak | |
| 7,526,966 B2 | 5/2009 | Gysling et al. | |
| 7,624,650 B2 | 12/2009 | Gysling et al. | |
| 8,286,466 B2 | 10/2012 | Gysling | |
| 8,408,049 B2 * | 4/2013 | Hurmuzlu | G01F 1/74 73/61.44 |
| 2006/0278016 A1 | 12/2006 | Froehlich et al. | |
| 2007/0044572 A1 * | 3/2007 | Davis | G01F 1/66 73/861.42 |
| 2009/0240453 A1 * | 9/2009 | Straub, Jr. | G01F 1/662 702/79 |
| 2012/0055239 A1 | 3/2012 | Sinha | |
| 2012/0055253 A1 | 3/2012 | Sinha | |

OTHER PUBLICATIONS

Salem Al-Lababidi, David MBA and Abdulmajid Addali (2012); Upstream Multiphase Flow Assurance Monitoring Using Acoustic Emission; pp. 217-251.

Professor Y. Yan Department of Electronics, University of Kent, Canterbury Tomography techniques for multiphase flow measurement; p. 63.

Lex Scheers (Hint Services, The Netherlands) and Arnstein Wee (MPM, Norway); Solutions for Reliable and Accurate Measurement of Water Production in Subsea Wet Gas Fields; pp. 1-23.

Mahmound Meribout, Nabeel Z. Al-Rawahi, Ahmed M. Al-Naamany, Ali Al-Bimani, Khamis Al-Busaidi and Adel Meribout; A Multisensor Intelligent Device for Real-Time Multiphase Flow Metering in Oil Fields; May 12, 2010; pp. 1-13.

Arnstein Wee and Lars Farestvedt; A Combined Multiphase and Wetgas Meter with In-Situ Sampling of Fluid Properties; May 2-5, 2011; pp. 1-23.

http://www.nauticalcharts.noaa.gov/csdl/svp.html; Nov. 2014.

International Search Report for PCT/US2015/013566, mailed Apr. 24, 2015.

* cited by examiner

APPARATUS, SYSTEM AND PROCESS FOR CHARACTERIZING MULTIPHASE FLUIDS IN A FLUID FLOW STREAM

CROSS-REFERENCE TO RELATED APPLICATIONS

The present application claims priority under 35 U.S.C. Section 119(e) to U.S. Provisional Patent Application No. 61/941,694, filed Feb. 19, 2014, and titled "Apparatus, System And Process For Characterizing Multiphase Fluids In A Fluid Flow Stream," the entire content of which is incorporated herein by reference.

FIELD OF THE INVENTION

The field of the invention relates to the measurement of multiphase fluid flow characteristics using acoustics.

BACKGROUND

In many industries, such as the production of oil and gas from underground reservoirs, produced fluids flow through thick-walled pipes. It is desirable to be able to characterize such fluids in a non-invasive and rapid manner. One useful characterization of produced fluids is the percentage of water, oil, sand and gas present in a flow stream in a pipe or conduit.

Wells sometimes produce oil, gas, and water simultaneously, in varying quantities. During the later life of oil and gas producing wells, water production typically increases substantially as a percentage of overall produced fluid. Water production in large quantities is undesirable. Water and oil must be separated, and a significant amount of energy is expended on the surface for water/oil separation processes. Furthermore, water takes up pipe volume that otherwise could contain oil or gas, and therefore is an economic detriment in the course of such oil and gas production operations. Produced water must be separated from the hydrocarbons and treated before it is released back into the environment. Water separation and treatment processes are time consuming, costly, and energy intensive.

One manner of investigating and characterization of the oil, gas, and water fraction of a multiphase stream involves acoustics, or sound waves. In a two phase fluid, such as an oil and water composition, sound speed and sound attenuation are related to the composition of the fluid. An "effective" speed of sound may be measured by an acoustic transmission or pulse echo process in a fluid mixture. In such a process, a sound or acoustic pulse of a certain duration may be created by an ultrasonic transducer that is attached to the outer wall of a pipe. The sound may be sent through the fluids in the pipe, and detected on the opposite side of the pipe by a receiving transducer. If the time of the acoustic pulse is determined, then sound speed may be calculated based upon the time and distance traveled, for a given temperature. Once that data is available, then an algorithm may be employed to determine an approximation of the oil and water percentages in the multiphase flow stream.

FIG. 1 shows a conventional prior art system 100 with one emitting and one receiving transducer. In the prior art system 100, an acoustic signal is transmitted from an emitting transducer 102 to a receiving transducer 104 across a fluid 106 that is in a pipe 108. In this prior art system 100, regions 110 represent only about 20% of the cross-sectional volume of the pipe 108 that is interrogated. The remaining 80% of the cross-sectional volume of the pipe 108 presents a region of undetected fluid that is not under examination by the acoustic signal traversing the fluid 106. In the prior art system 100, the accuracy of results obtained is limited by the scope of analysis with respect to the total volume of multiphase flow within the pipe 108.

FIGS. 2 and 3 show results from numerical finite element analysis of the prior art system 100. In FIGS. 2 and 3, areas 202, 302 illustrate that a relatively small amount of the total fluid 200 flowing through the pipe 108 of FIG. 1 is interrogated by the prior art system 100.

There is a continuing need in the industry to improve the accuracy of multiphase fluid characterization. The present disclosure is directed towards improved apparatus, systems, and processes for evaluating and determining the characteristics of multiphase fluid flow in a pipe or conduit. Such characteristics may include the water, sand oil and/or gas percentages in the multiphase fluid flowing through the pipe or conduit.

SUMMARY

The invention comprises an apparatus, system and process for characterizing multiphase fluids in a fluid flow stream. In an example embodiment, a system for determining characteristics of a multiphase fluid includes pipe and multiple pairs of transducers positioned circumferentially around the pipe. Each pair of transducers includes a transmitting transducer and a receiving transducer. The transmitting transducer of each pair of transducers is oriented to transmit a respective acoustic signal toward the receiving transducer of the pair of transducers. The transmitting transducer of each pair of transducers is operable to transmit the respective acoustic signal sequentially with respect to other transmitting transducers of the multiple pairs of transducers. A reception of a first acoustic signal transmitted by a transmitting transducer of a first pair of transducers of the multiple pairs of transducers is completed by a receiving transducer of the first pair transducers before a transmitting transducer of another pair of transducers of the multiple pairs of transducers transmits a second acoustic signal.

In another example embodiment, a system for measuring characteristics of a multiphase fluid includes an inner pipe and an outer pipe. The inner pipe is positioned within the outer pipe, and the inner pipe and the outer pipe define an annular space. The system further includes a plurality of transducers positioned circumferentially around the inner pipe. Each transducer is configurable to operate as a transmitting transducer and a receiving transducer. Each transducer is oriented to transmit an acoustic signal toward the outer pipe such that the acoustic signal is reflected off the outer pipe toward the transducer for reception by the transducer.

In yet another example embodiment, a method for determining characteristics of a multiphase fluid includes transmitting a first acoustic signal by a first transmitting transducer and receiving the first acoustic signal by a first receiving transducer. The method further includes transmitting a second acoustic signal by a second transmitting transducer after receiving the first acoustic signal by the first receiving transducer. The method also includes receiving the second acoustic signal by a second receiving transducer. Further, the method includes determining a travel time of the first acoustic signal through a first portion of a multiphase fluid and determining a travel time of the second acoustic signal through a second portion of the multiphase fluid. The first transmitting transducer, the first receiving transducer, the second transmitting transducer, and the second receiving transducer are positioned circumferentially around the pipe.

These and other aspects, objects, features, and embodiments will be apparent from the following description and the appended claims.

BRIEF DESCRIPTION OF THE DRAWINGS

Reference will now be made to the accompanying drawings, which are not necessarily drawn to scale, and wherein.

Figure 1:
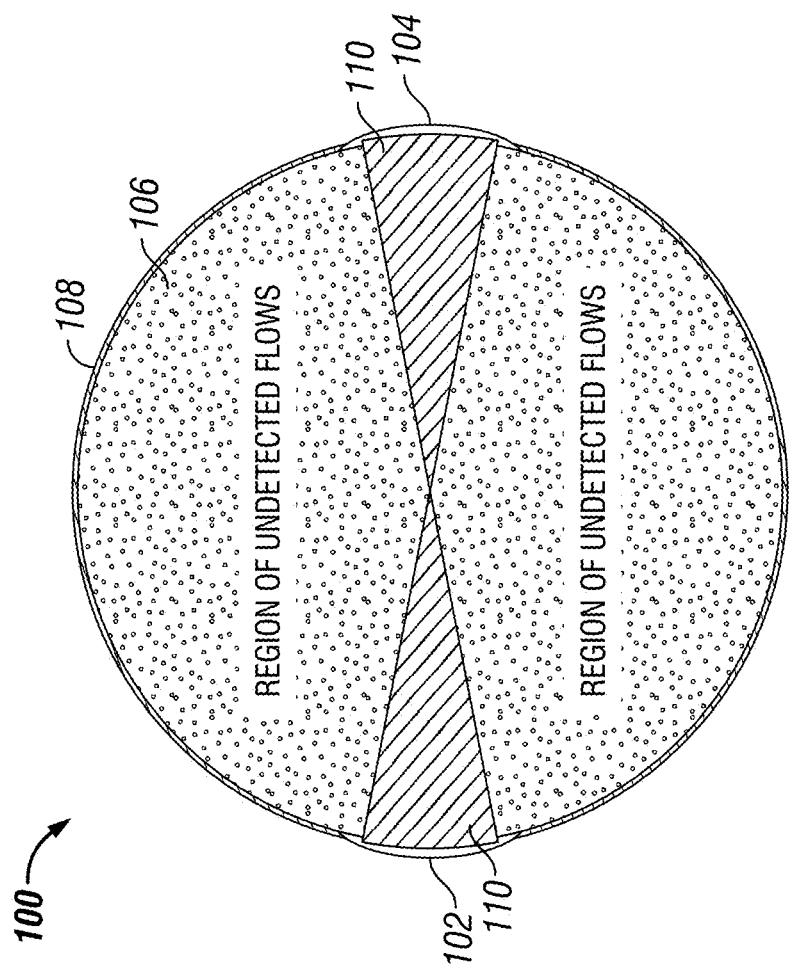
FIG. 1 shows a conventional prior art system with one emitting and one receiving transducer.
Figure 2:
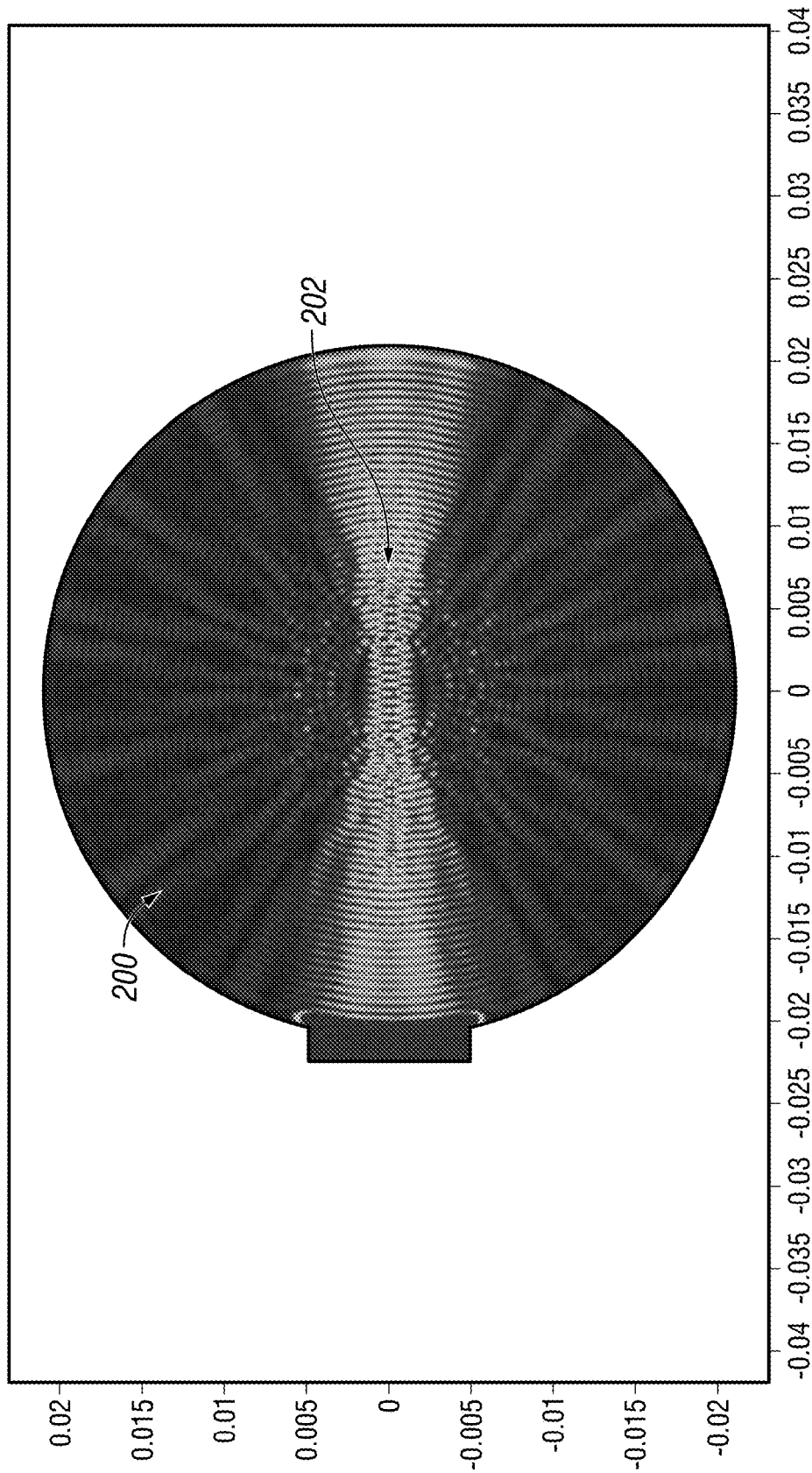
FIGS. 2 and 3 illustrate results from numerical finite element analysis of the prior art system 100 of FIG. 1.
Figure 3:
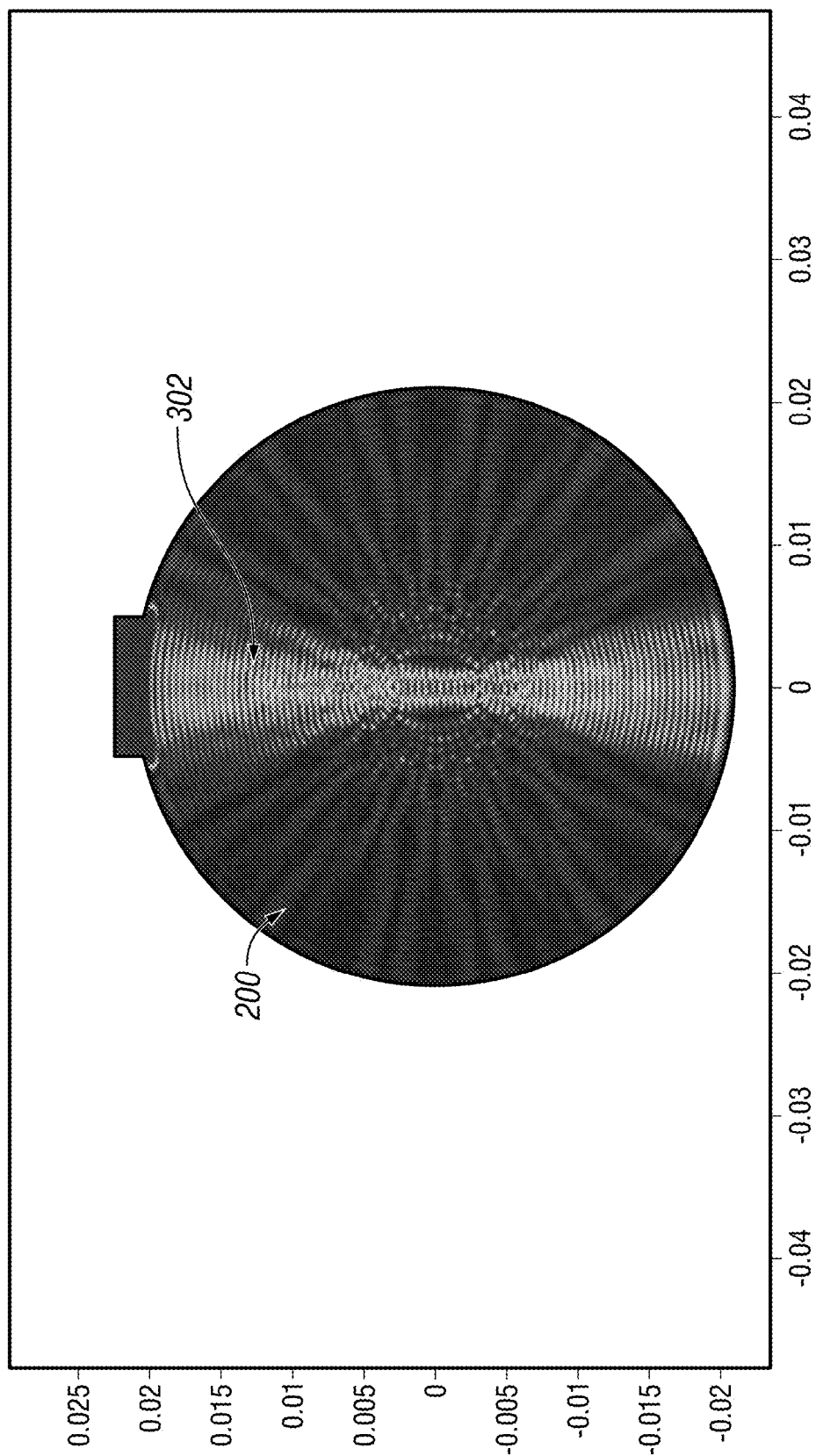

The drawings illustrate only example embodiments and are therefore not to be considered limiting in scope. The elements and features shown in the drawings are not necessarily to scale, emphasis instead being placed upon clearly illustrating the principles of the example embodiments. Additionally, certain dimensions or placements may be exaggerated to help visually convey such principles. In the drawings, reference numerals designate like or corresponding, but not necessarily identical, elements.

DETAILED DESCRIPTION OF THE EXAMPLE EMBODIMENTS

In a multiphase (e.g., two phase) fluid such as an oil and water composition, sound speed and sound attenuation are related to the composition of the fluid. Sound speed through the fluid may be measured by an acoustic transmission or pulse echo process. For example, an acoustic pulse of a given duration may be created by a transducer that is attached to the wall of a pipe. To illustrate, sound from a transmitting transducer may be sent through a multiphase fluid flowing through a pipe and detected by a receiving transducer that is disposed on the pipe diametrically opposite the transmitting transducer. Alternatively, sound from a transducer may be sent through a multiphase fluid flowing through an annulus and received by the same transducer after the sound is reflected back to the transducer. If the time of travel of the acoustic pulse through the multiphase fluid is determined, then sound speed can be calculated based upon the time and distance traveled for a given temperature of the fluid. The sound speed may be correlated to known data to determine the characteristics of the fluid including the composition of the multiphase flow stream.

In general, "tomography" refers to imaging by sections or sectioning, through the use of a penetrating wave. A device used in tomography is called a tomograph, while the image produced is a tomogram. In some embodiments, multiple cylindrically focused ultrasound transducers may be employed.

Figure 4:
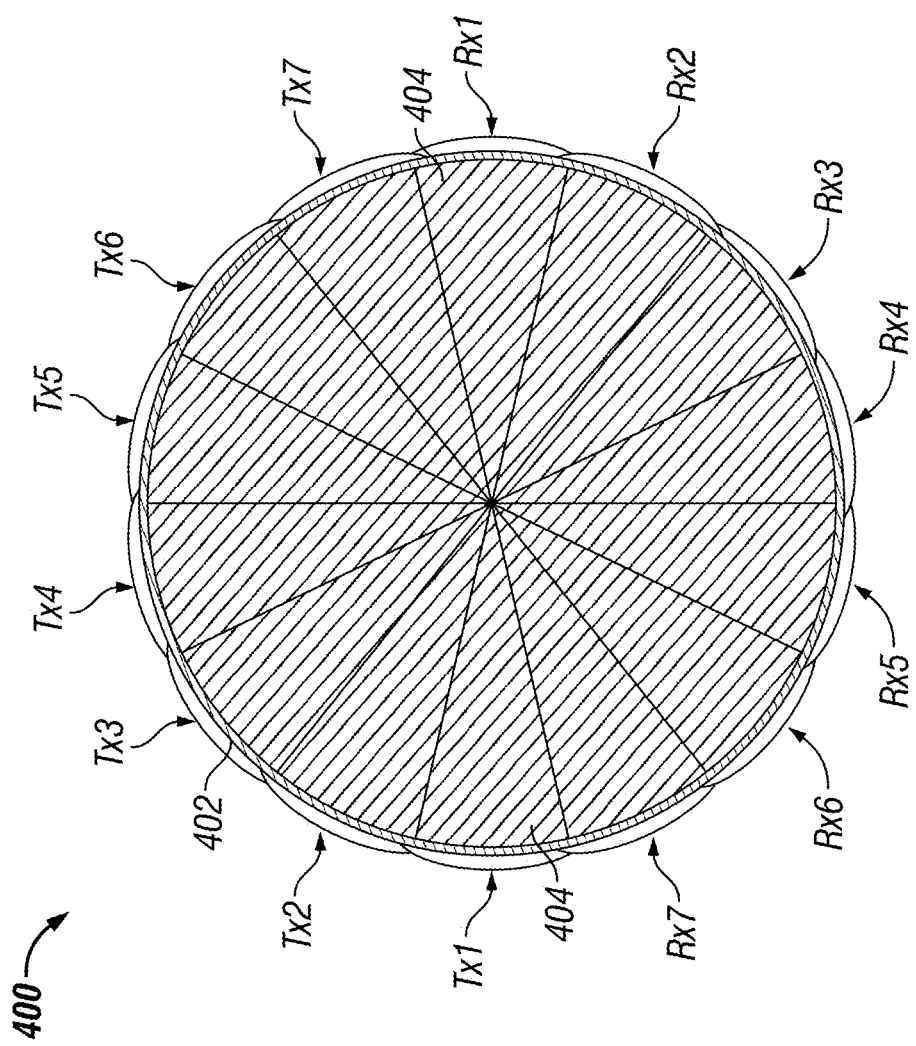
FIG. 4 illustrates a system of multiple transducers that are positioned circumferentially around a pipe according to an example embodiment.

FIG. 4 illustrates a system 400 of multiple transducers Tx1-Tx7, Rx1-Rx7 that are positioned circumferentially around a pipe 402 according to an example embodiment. As illustrated in FIG. 4, multiple transducers Tx1-Tx7, Rx1-Rx7 may be used around a cylindrical pipe to transmit or receive acoustic signals through segments of the fluid in all directions, i.e. from zero to 360 degrees, to cover substantially the entire horizontal cross-sectional of the fluid in the pipe 402. In some example embodiments, the transducers Tx1-Tx7, Rx1-Rx7 may generally be in a horizontal plane.

In some example embodiments, the transmitting transducers Tx1-Tx7 are piezoelectric transducers that can each receive an electrical signal and generate an acoustic signal, and the receiving transducers Rx1-Rx7 are piezoelectric transducers (e.g., Lead Zirconate Titanate piezoelectric transducers) that can each receive an acoustic signal and generate an electrical signal. The transducers Tx1-Tx7, Rx1-Rx7 are positioned circumferentially around a wall of the pipe 402. For example, the transducers Tx1-Tx7, Rx1-Rx7 may be attached to the outside surface of the pipe wall and may not be in direct contact with the multiphase fluid in the pipe 402. Alternatively, a portion of each transducer Tx1-Tx7, Rx1-Rx7 may be exposed to the fluid flowing through the pipe 402 via a respective opening in the pipe 402.

Each one of the transducers Tx1-Tx7 is operable to transmit an acoustic signal based on an electrical signal provided to the respective transducer, and each one of the receiving transducers Rx1-Rx7 is operable to receive an acoustic signal and output a respective electrical signal. Individual transducers Tx1-Tx7 may be paired with individual receiving transducers Rx1-Rx7 to transmit and receive acoustic signals. For example, the transducer Tx1 may be paired with the receiving transducer Rx1, and the transducer pair Tx2 may be paired with the receiving transducer Rx2. In general, each transmitting transducer Tx1-Tx7 may be paired with one of the receiving transducers Rx1-Rx7 to form a transducer pair Tx-Rx. To illustrate, in each pair of transducers Tx-Rx, the transducer Tx may be oriented to transmit an acoustic signal toward the receiving transducer Rx, and the receiving transducer Rx may be oriented to receive the acoustic signal from the transmitting transducer Tx. For example, the transmitting transducer Tx1 may be positioned on the wall of the pipe 402 diametrically opposite the receiving transducer Rx1 and transmit an acoustic signal toward the receiving transducer Rx1. The other pairs Tx-Rx of transmitting and receiving transducers may be oriented and operate in a similar manner.

The acoustic signals transmitted by the transmitting transducer Tx1-Tx7 and received by the receiving transducer Rx1-Rx7 traverse sections of the volume of the pipe 402. To illustrate, an area 404 represents an illustrative cross-sectional area of a fluid that is traversed by the acoustic signal transmitted by the transmitting transducer Tx1 and received by the receiving transducer Rx1. The area 404 is narrow near the radial center of the pipe 402, illustrating the focusing effect to the cylindrical pipe 402 on the acoustic signal transmitted by the transmitting transducer Tx1. Acoustic signals from the other transmitting transducer Tx2-Tx7 traverse the fluid in a similar manner. The transducers Tx1-Tx7 are operable to transmit acoustic signals sequentially with respect to each other as described below. The combined area of the fluid traversed by the acoustic signals from the transducer Tx1-Tx7 and received by the receiving transducers Rx1-Rx7 results in a more complete interrogation of the fluid as compared to the interrogation provided by a single pair of transducers.

Although the pipe 402 is cylindrical as shown in FIG. 4, in alternative embodiments, the pipe 402 may be polygonal. For example, the pipe 402 may have a rectangular or hexagonal cross-section. Although a particular arrangement of the transducers Tx1-Tx7 and Rx1-Rx7 is shown in FIG. 4, in alternative embodiments, the transducers Tx1-Tx7 and Rx1-Rx7 may be arranged in a different configuration without departing from the scope of this disclosure. Further, although seven transmitting transducers and seven receiving transducers are shown in FIG. 4, in alternative embodiments, fewer or more than seven of each transducer type may be used. Further, each one of the transmitting transducers Tx1-Tx7, Rx1-Rx7 may be configurable to operate as a transmitting or receiving transducer.

Figure 5:
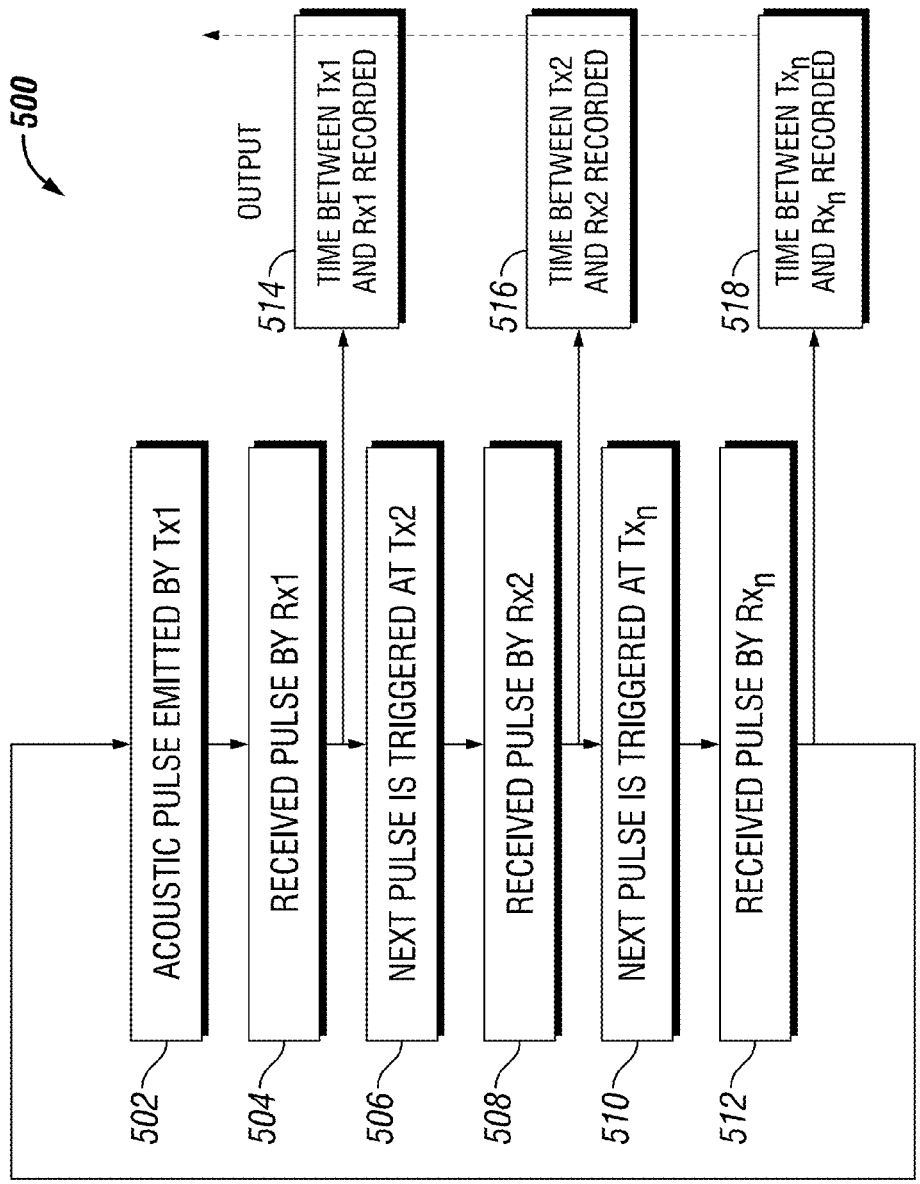
FIG. 5 illustrates a sequence of operation of multiple transducers such as the transducers of FIG. 4 according to an example embodiment.

FIG. 5 illustrates a sequence of operation of multiple transducers such as the transducers Tx1-Tx7, Rx1-Rx7 of FIG. 4 according to an example embodiment. Referring to FIGS. 4 and 5, in some example embodiments, the transmitting transducers Tx1-Tx7 may be pulsed sequentially with a time delay relative to the immediately prior transmitting transducers. To illustrate with respect to sequential operations of transducer pairs, a first acoustic signal transmitted by the transmitting transducer Tx1 of the transducer pair Tx1-Rx1 is received by the receiving transducer Rx1 before one of the other transmitting transducers Tx2-Tx7 transmits an acoustic signal toward a corresponding one of the receiving transducers Rx2-Rx7. After the process of transmission and reception using the transducer pair Tx1-Rx1 is completed, another transducer pair may be operated in a similar manner as transducer pair Tx1-Rx1.

To illustrate the sequence of operation of the transducer pairs Tx-Rx with reference to FIGS. 4 and 5, the transducer Tx1 first emits/transmits an acoustic pulse at step 502 of FIG. 5. The acoustic pulse traverses the multiphase fluid flowing through the pipe 402 and is received by the receiving transducer Rx1 at step 504. The time between the transmission at step 502 and the reception at step 504 may be recorded or otherwise processed at step 514. After step 504, the next acoustic pulse is triggered/transmitted at step 506 by the transducer Tx2.

In some example embodiments, the transducer Tx2 transmits the acoustic pulse toward the transducer Rx2 immediately after a determination that the acoustic pulse transmitted by the transducer Tx1 is received by the transducer Rx1. For example, the transducer Tx2 may transmit the acoustic pulse toward the transducer Rx2 without waiting for step 514 to be performed. In some example embodiments, a delay time may be allowed to elapse between a determination of acoustic pulse reception by the transducer Rx1 and the transmission of an acoustic signal by the transducer Tx2. Further, reflective echo signals resulting from current or prior acoustic pulses may be disregarded in a manner known to those of ordinary skill in the art.

Figure 7:
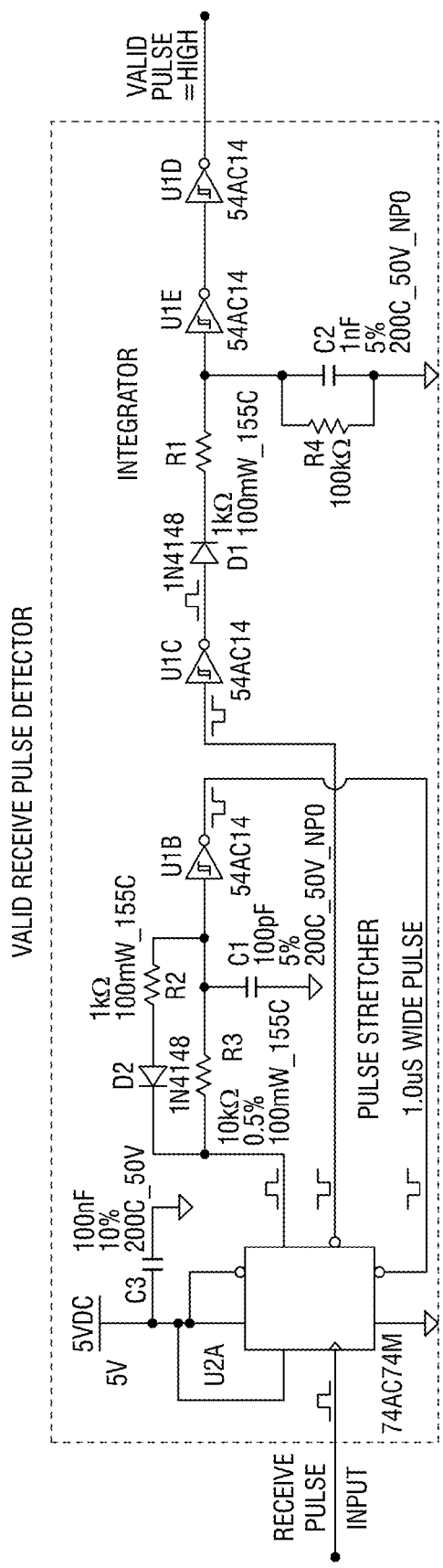
FIG. 7 illustrates circuitry of the system of FIG. 6 used in re-attempting a successful operation by a transducer pair according to an example embodiment.
Figure 8A:
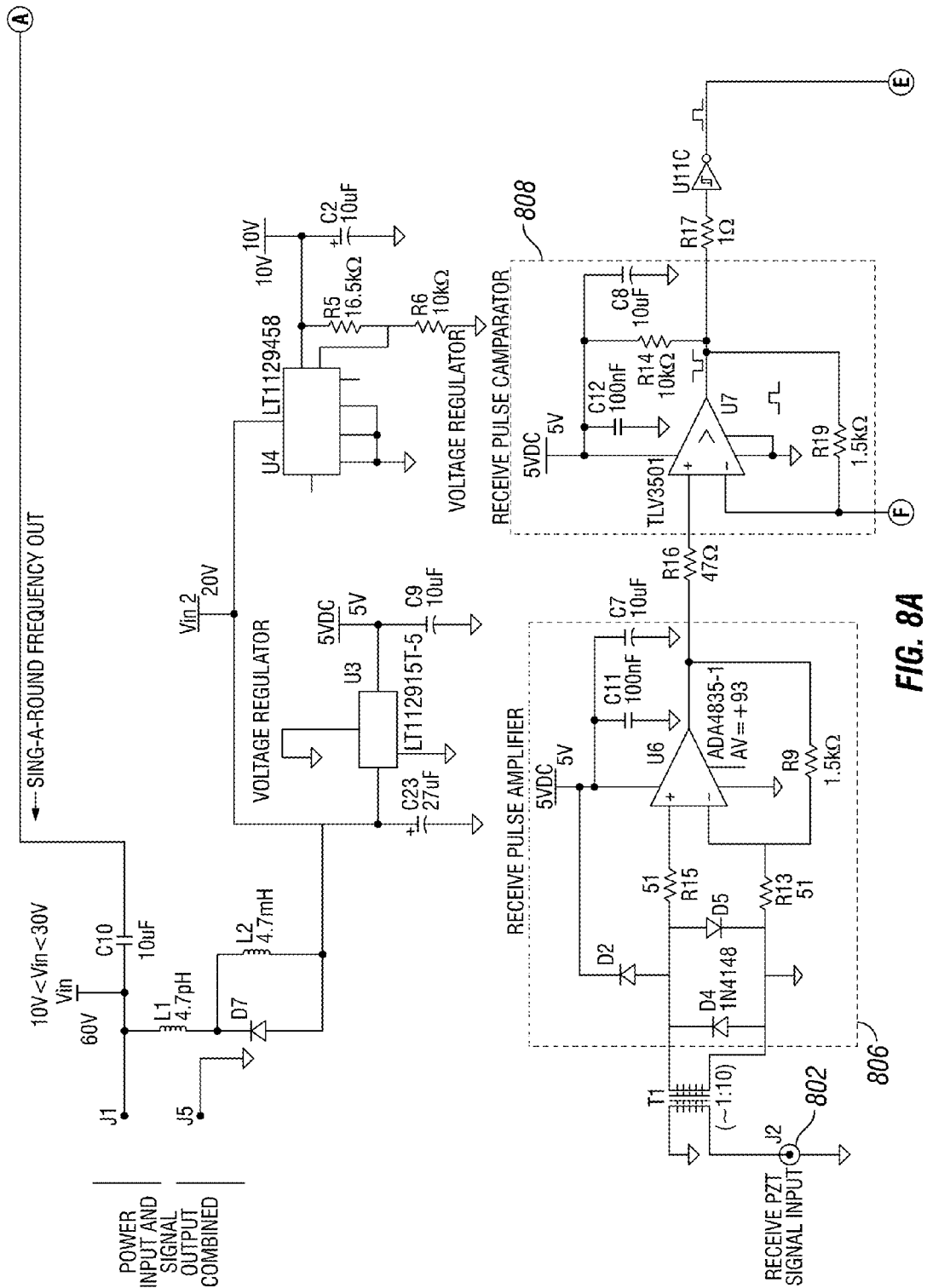
FIGS. 8A-AD illustrate circuitry of a sing-around core of the system of FIG. 6 according to an example embodiment.
Figure 8B:
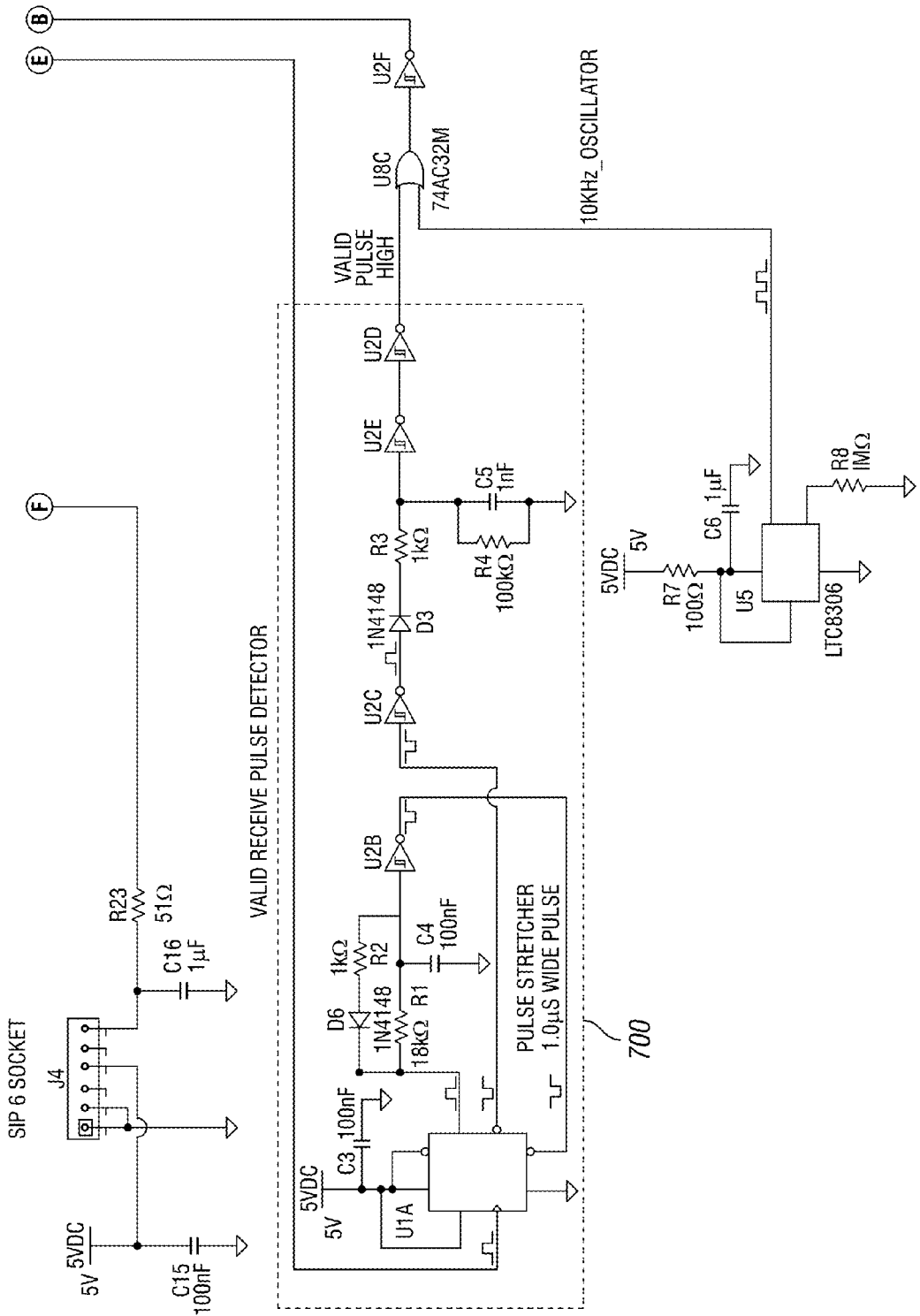
Figure 8C:
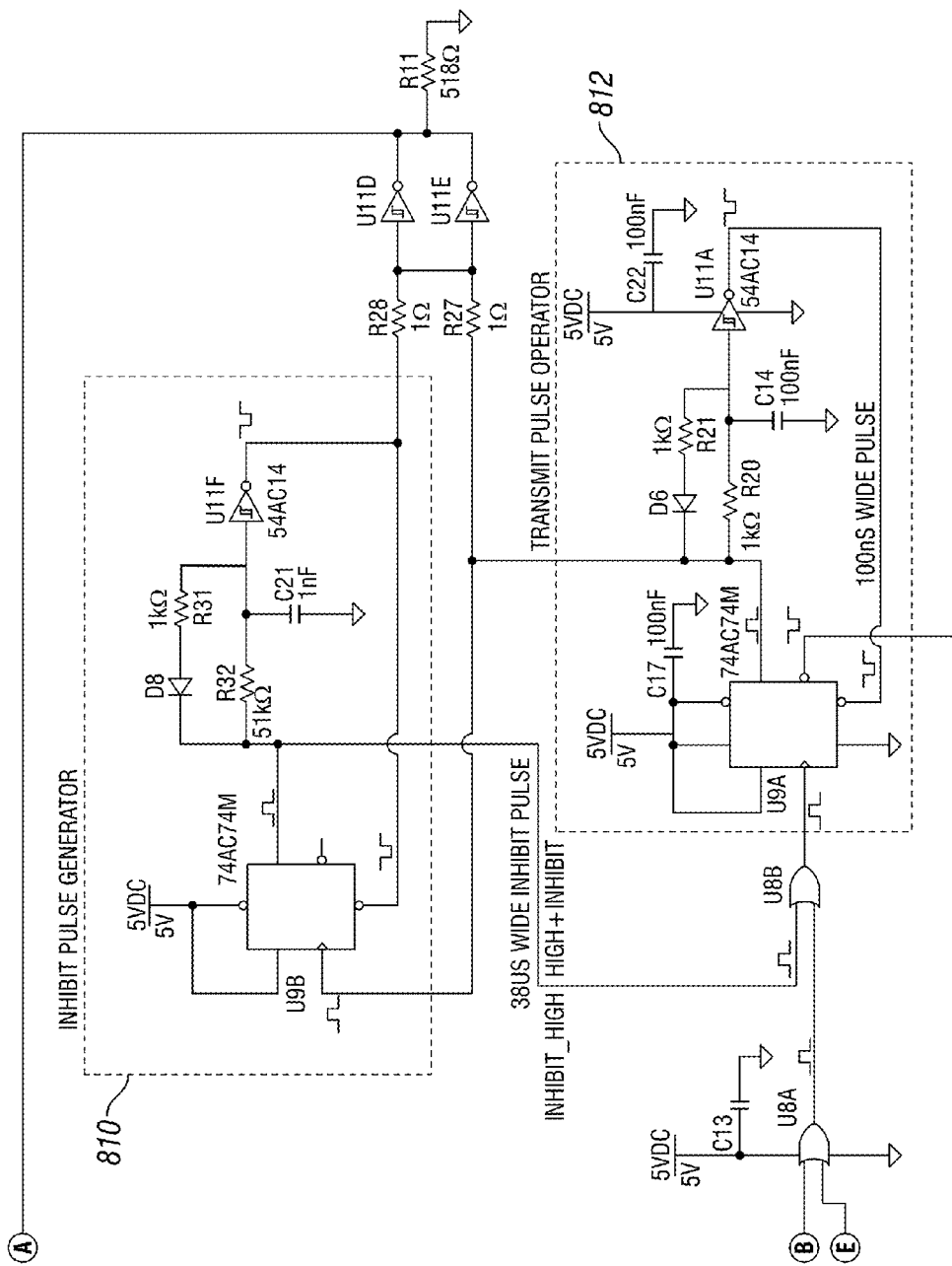
Figure 8D:
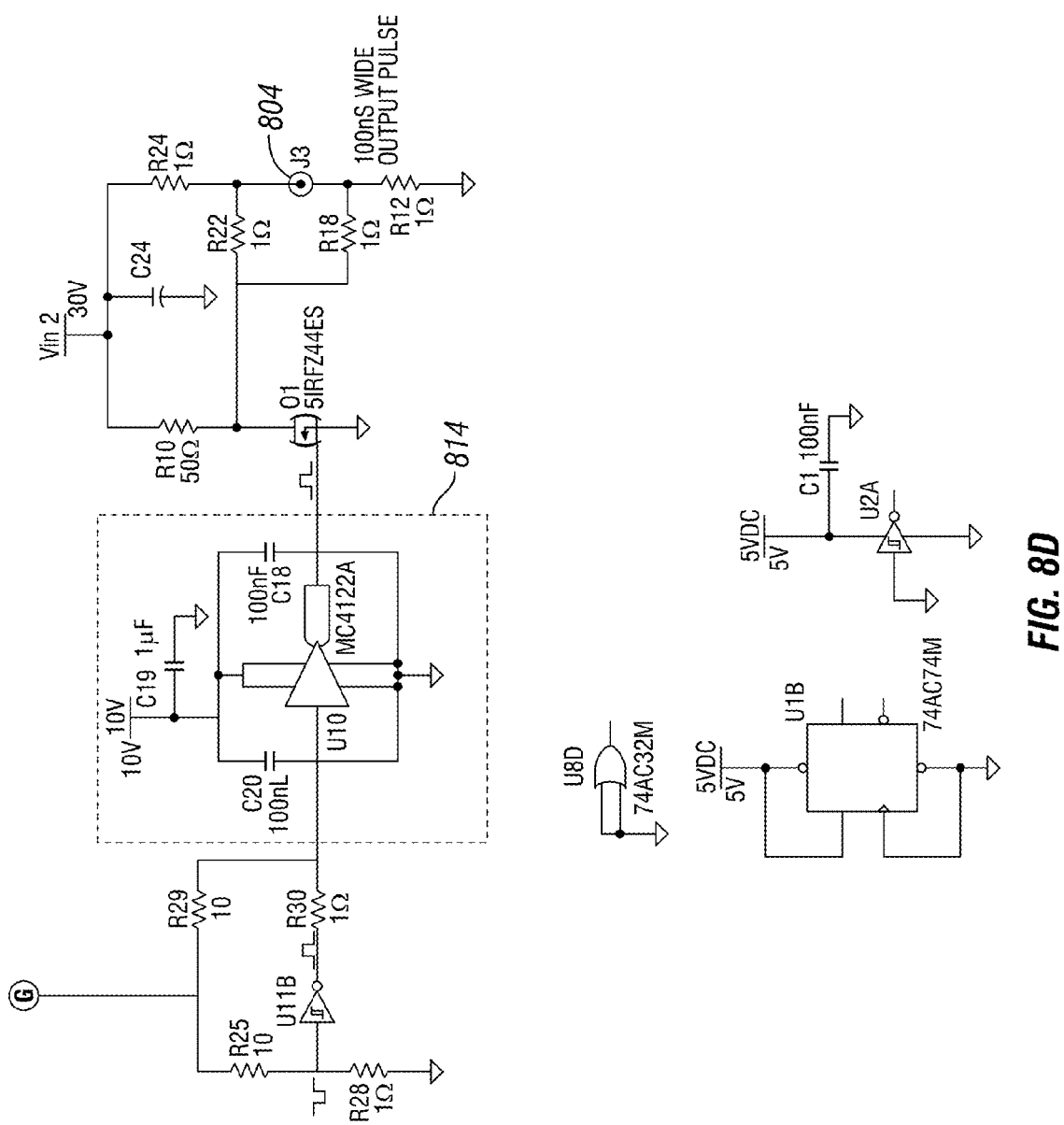

In some example embodiments, if a first acoustic pulse transmitted by the transducer Tx1 is not successfully received by the transducer Rx1, the transducer Tx1 may periodically reattempt transmitting another acoustic pulse until successful reception before the transducer Tx2 transmits an acoustic signal toward the transducer Rx2. The transducer Tx2 transmits the acoustic pulse toward the transducer Rx2 after an acoustic pulse transmitted in the reattempt by the transducer Tx1 is successfully received by the transducer Rx1. Similarly, each one of the other transducers Tx2-Txn may be capable of reattempting transmission of an acoustic pulse. An example circuit that is used in the implementation reattempting transmission of acoustic signals is shown in FIG. 7.

Continuing with the sequential operation of the transducer pairs of FIGS. 4 and 5, at step 508, the acoustic pulse transmitted by the transducer Tx2 is received by the transducer Rx2. At step 516, the time between the transmission and the reception of the acoustic pulse at steps 506, 508 may be recorded or otherwise processed. After step 508, following the reception of the acoustic pulse transmitted by the transducer Tx2, other transducer pairs (e.g., Tx3-Rx3, Tx4-Rx4, . . . ) including transducer pairs Txn-Rxn (where n is an integer great than 2) operate sequentially in a similar manner described above to interrogate the fluid flowing through the pipe 402. Similar to steps 514, 516, the time between the transmission and reception of the acoustic pulses at the other transmission and reception steps may be recorded or otherwise processed. For example, at step 518, the time between the transmission and the reception of the acoustic pulse at steps 510, 512 may be recorded or otherwise processed.

Because an acoustic pulse is generally transmitted following a successful reception of an immediately prior acoustic pulse, the time between sequential transmissions of acoustic pulses by the different transmitting transducers Tx1-Rxn depends on the time of travel of the acoustic pulses through the fluid from the transmitting transducers Tx1-Txn to the receiving transducer Rx1-Rxn.

In some example embodiments, the sequence of transducer pairs Tx-Rx may be selected to minimize interference among the transducer pairs. To illustrate, the transmitting transducer Tx1 may be spaced from the next transmitting transducer to reduce interference by the acoustic signal from the transducer Tx1. For example, after the process of transmission and reception using the transducer pair Tx1-Rx1 is completed, the transducer Tx5, which is roughly 90 degrees from the transducer Tx1 as shown in FIG. 4, may be operated instead of the transducer Tx2 to interrogate the fluid in the pipe 402. After the operation using the transducer pair Tx5-Rx5 is completed, another transducer pair (e.g., the transducer pair Tx3-Rx3 instead of transducer pair Tx4-Rx4) may be operated in a similar manner. The process of operation the different transducer pairs Tx-Rx may continue in a similar manner until all transducer pairs have been sequentially operated to interrogate the fluid flowing through the pipe 402. After a full cycle of operating the transducer pairs Tx-Rx is completed, the cycle may be repeated in the same or different sequence of the transducer pairs. In some example embodiments, the times recorded and/or processed at steps 514, 516, 518 may be provided as output for further processing. For example, Fast Fourier Transform and other methods may be implemented on the data conveying the recorded or processed time information.

Once the time of travel of the acoustic pulses through the multiphase fluid is determined, then speed of sound in the multiphase fluid can be calculated based upon the travel time and distance traveled for a given temperature of the fluid. The distance traveled through the multiphase fluid by an acoustic pulse is approximately the distance between the transmitting and receiving transducers of a transducer pair Tx-Rx. Once determined, the speed of sound through the multiphase fluid may be correlated to known data to determine the characteristics of the multiphase fluid including the composition of the multiphase fluid.

By using multiple transducer pairs Tx-Rx, a more complete interrogation of the multiphase fluid is achieved as compared to a system that implements a single pair of transducers. Because of the sequential operation of the multiple transducer pairs Tx-Rx, interference among acoustic signals transmitted by the multiple transmitting transducers Tx1-Rxn is kept low.

Figure 6:
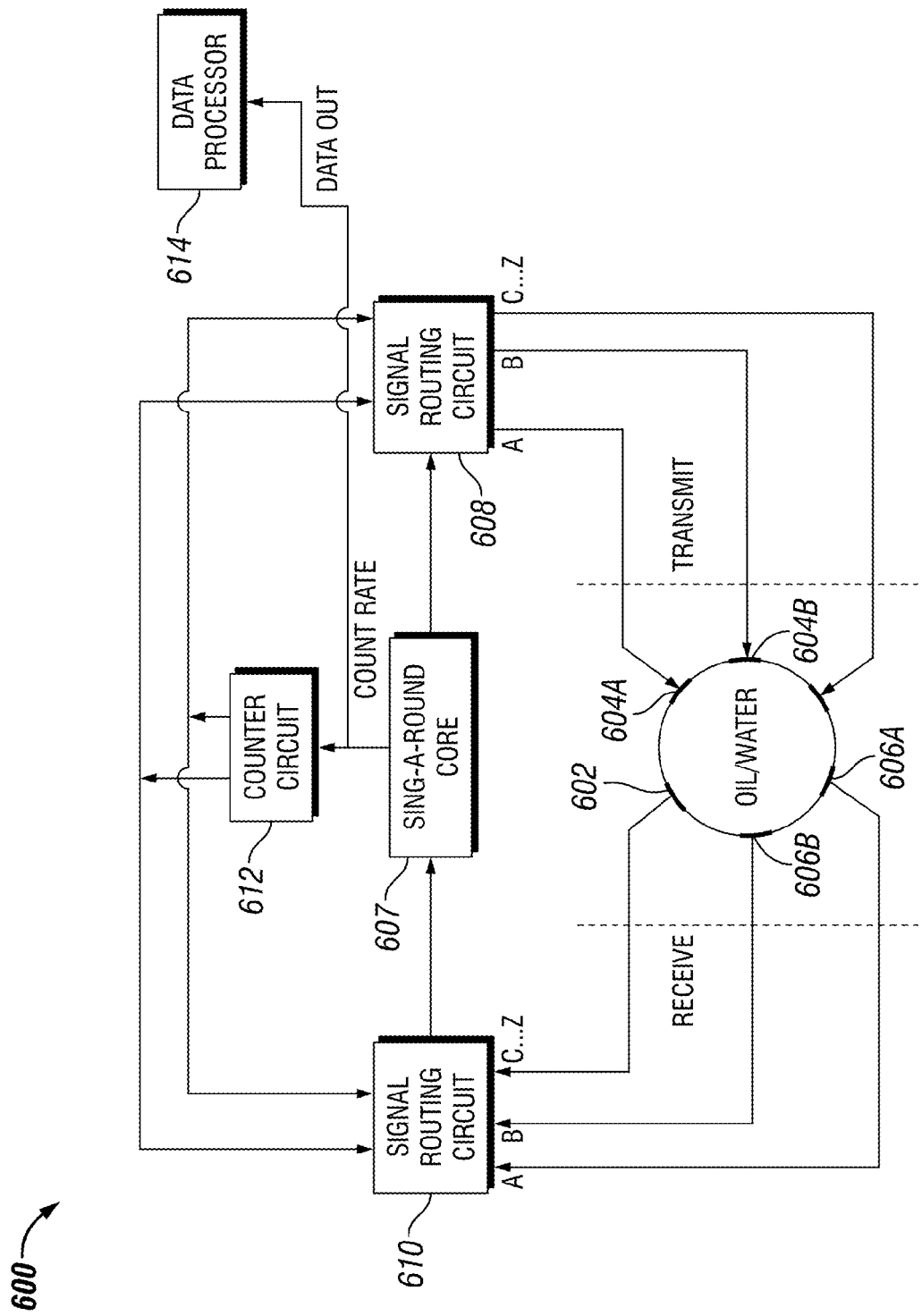
FIG. 6 illustrates a block diagram of a system for multiphase fluid flow measurement that is based on a sing-a-round core and multiple transducers such as shown in FIG. 4 according to an example embodiment.

FIG. 6 illustrates a block diagram of a system 600 for multiphase fluid flow measurement that is based on a sing-a-round core 607 and multiple transducers such as shown in FIG. 4 according to an example embodiment. In some example embodiments, the system 600 may be used to implement the operations shown in and described with respect to FIG. 5. In general, components of the system 600 are designed to operate at temperatures above 85 degrees Celsius. For example, the system 600 may be implemented in an oil/gas operation downhole environment.

As shown in FIG. 6, the system includes a pipe 602, which may be the same or similar to the pipe 402 of FIG. 4. In some example embodiments, the system 600 includes a sing-a-round core 607 that controls some operations of the system 600. For example, the sing-a-round core 607 may be a signal processing device. The system 600 also includes a signal routing circuit 608, a signal routing circuit 610, and a counter 612. Multiple transducers including transmitting transducers 604A, 604B, . . . and receiving transducers 606A, 606B, . . . are circumferentially attached to the pipe 602. For example, the transmitting transducer 604A and the receiving transducer 606A operate as a pair where the transmitting transducer 604A is positioned and oriented to transmit an acoustic signal toward the receiving transducer 606A. Similarly, the transmitting transducer 604B and the receiving transducer 606B operate as a pair where the transmitting transducer 604B is positioned and oriented to transmit an acoustic signal toward the receiving transducer 606B. The transducers 604A, 604B, 606A, 606B, . . . may be attached on the outside surface of the pipe 602 without exposure to the fluid flowing through the pipe 602. Alternatively, the transducers 604A, 604B, 606A, 606B, . . . may be exposed to the fluid via openings in the wall of the pipe 602 as more clearly shown in FIG. 15.

During operation of the system 600, an acoustic pulse is generated by one of the transmitting transducers and traverses the multiphase fluid flowing within the pipe 602. The acoustic pulse may be received and used to increment the counter 612 and to initiate a new acoustic pulse. The cycle of generation and reception of acoustic pulses may be repeated indefinitely by sequentially changing the transmitting and receiving transducer pairs. The system frequency, which corresponds to the frequency of the acoustic pulse generation, may be determined from the count rate of the counter 612 and depends on the average acoustic (e.g., ultrasonic) transit time of the acoustic pulses through the fluid.

An estimate can be made of the speed of the ultrasonic signal in the fluid, provided the sample thickness (that is distance traveled by the ultrasonic signal, which corresponds to the distance between a transmitting transducer and a receiving transducer) and electronic circuit delays are known. By employing multiple transducers as shown in FIGS. 4 and 6 at multiple locations around the periphery of a pipe containing a multiphase fluid and operation the transducers sequentially, characteristics of the fluid including the composition of the fluid in the pipe may be determined by reference to known acoustic pulse speeds in water, oil, or gas at a given sample temperature and with a higher level of accuracy than by simply using a single pair of transducers as shown in FIG. 1.

To illustrate the operation of the system 600 with respect to transducer pairs 604A/606A, 604B/606B, . . . , during operation, the sing-a-round core 607 provides an electrical signal (e.g., a pulse) to the signal routing circuit 608. The electrical signal from the sing-a-round core 607 is provided to one of the transmitting transducers 604A, 604B, . . . at a time based on the selection signals from the counter 612. For example, the signal routing circuit 608 provides the electrical signal from the sing-a-round core 607 only to the transmitting transducer 604A via output A if the selection signals from the counter 612 are in a first state. Similarly, the signal routing circuit 608 provides the electrical signal from the sing-a-round core 607 to only the transmitting transducer 604B via output B if the selection signals from the counter 612 are in second state. In general, changes in the signals from the counter 612 may result in sequential activation of only one transmitting transducer of the transmitting transducers 604A, 604B, . . . at a time via the outputs A, B, C, . . . , Z of the signal routing circuit 608. The frequency of change in the selection signals from the counter 612 is controlled by the sing-a-round core 607 and depends on the travel time of acoustic signals transmitted by the transmitting transducers 604A, 604B, . . . through the multiphase fluid (e.g., oil/water) flowing through the pipe 602.

Each transmitting transducer 604A, 604B, . . . that receives the electrical signal from the sing-a-round core 607 via the signal routing circuit 608 transmits an acoustic signal toward a respective one of receiving transducer 606A, 606B, . . . as described above. For example, the transmitting transducers 604A may transmit a first acoustic signal toward the receiving transducer 606A, and the transmitting transducers 604B may transmit a second acoustic signal toward the receiving transducer 606B after the first acoustic signal is received by the transducer 606A. In some example embodiments, the signal from the sing-a-round core 607 provided to the signal routing circuit 608 is amplified before it is provided to the transmitting transducers 604A, 604B, . . . via outputs A, B, C, . . . Z.

In some example embodiments, the receiving transducers 606A, 606B, . . . sequentially receive a respective acoustic signal transmitted by the respective transmitting transducer 604A, 604B, . . . through the multiphase fluid. Each one of the receiving transducers 606A, 606B, . . . generates a respective electrical signal that is provided to the sign-a-round core 607 via the signal routing circuit 610. The electrical signals from the receiving transducers 606A, 606B, . . . are provided to the signal routing circuit 610 via inputs A, B, C, . . . , Z. The signal routing circuit 610 sequentially provides the electrical signals from the receiving transducers 606A, 606B, . . . one at a time to the sing-a-round core 607 based on the selection signals from the counter 612. After an electrical signal is received from one of the receiving transducer 606A, 606B, . . . via the signal routing circuit 610, the next transmitting transducer is activated by the electrical signal from the sing-a-round core 607 via the signal routing circuit 608. By sequentially activating the transmitting transducers 604A, 604B, . . . to transmit acoustic signals through the multiphase fluid and sequentially providing the electrical signals generated by the receiving transducers 606A, 606B, . . . to the sing-a-round core 607, the multiphase fluid flowing through the pipe 602 may be interrogated based on the travel times of the acoustic signals through multiphase fluid. As described above, a transmitting transducer 604A, 604B, . . . is activated to transmit an acoustic signal only after an immediately prior acoustic signal transmitted by another one of the transmitting transducers 604A, 604B, . . . is successfully received by a corresponding one of receiving transducers 606A, 606B, . . . .

As shown in FIG. 6, the counter 612 may be incremented based on a signal (count rate) from the sing-around-core 607. The count rate signal provided to the counter 612 may also be provided as an output, for example, to a data processing device 614. The count rate signal may indicate transmission times of the acoustic signals through the multiphase fluid flowing through the pipe 602. Methods such as Fast Fourier Transform ("FFT") may be used to transform the count rate output and other signals from the sing-around-core 607 into the frequency domain for further processing and analysis. In some example embodiments, delays through electronic and other components of the system 600 may be accounted for in determining the travel times of acoustic pulses through the multiphase fluid flowing through the pipe 602.

In some example embodiments, electrical signal other than electrical pulses may be provided to the transducers to generate acoustic signals. Further, the electrical signals provided by the sing-a-round core 607 to the different transmitting transducers 604A, 604B, . . . via the decoder input selector 608 may have different characteristics (e.g., different amplitudes, pulse width, etc.) from each other. Accordingly, the acoustic signals transmitted by the different transducers may have different characteristics that may be used in characterizing the fluid flowing through the pipe 602.

FIG. 7 illustrates a Valid Receive Pulse Detector circuitry 700 of the system 600 of FIG. 6 used in re-attempting a successful operation by a transducer pair according to an example embodiment. As described above, when an acoustic signal transmitted by a transmitting transducer (e.g., transmitting transducer 604A) of a transducer pair (e.g., the transducer pair 604A/606A) is not successfully received by the receiving transducer (e.g., the receiving transducer 606A) of the transducer pair, the transmitting transducer may reattempt to transmit an acoustic signal to the receiving transducer.

In some example embodiments, the circuitry 700 is implemented in the sing-around-core 607 of FIG. 6 and together with the other components of the system 600 may enable the transmitting transducer to automatically reattempt transmitting an acoustic signal to the receiving transducer. For example, an acoustic signal may be transmitted automatically in a reattempt by a transmitting transducer when a first acoustic signal transmitted by the transmitting transducer was not successfully received by a receiving transducer during a time that the first acoustic signal is expected to propagate through the multiphase fluid and reach the receiving transducer.

To illustrate, the Valid Receive Pulse Detector circuitry 700 switches to a built in an oscillator (e.g., a 10 KHz oscillator), which triggers a transmitting transducer continuously until the corresponding receiving transducer successfully receives the acoustic pulse transmitted by the transmitting transducer. Further, the presence of the oscillator output signal (e.g., a 10 KHz signal) serves as an indicator that something (e.g., an air pocket or a solid block) is stopping the transmission of the acoustic signal through the fluid.

FIGS. 8A-8D illustrate circuitry of the sing-around core 607 of the system 600 of FIG. 6 according to an example embodiment. Referring to FIGS. 6 and 8A-8D, the electrical signals from the receiving transducers are sequentially provided to the sing-around core 607 via an Input port 802 of the sing-around core 607 and an output pulse is provided by the sing-around core 607 via Output port 804. The primary blocks of the sing-around core 607 include a Receive Pulse Amplifier 806, a Receive Pulse Comparator 808, the Valid Receive Pulse Detector 700 shown in FIG. 7, an Inhibit Pulse Generator 810 that may be used to delay generation of a pulse, a Transmit Pulse Generator 812, and a driver 814 that is used to provide current and/or voltage gain.

In operation, a signal at the Input port 802 is amplified by the Receive Pulse Amplifier 806. The amplified output signal from the Receive Pulse Amplifier 806 is provided to the Receive Pulse Comparator 808, which produces an output signal when the level of the signal from the Receive Pulse Amplifier 806 exceeds a certain threshold. The output signal from the Receive Pulse Comparator 808 triggers the Transmit Pulse Generator 812 (essentially a one shot circuit) which generates a brief output pulse (e.g., 100 to 200 ns long). The brief pulse is used to trigger an inhibit pulse (e.g., 30 to 40 us) (time related to the pipe diameter) by the Inhibit Pulse Generator 810, which is used to prevent further triggering by the output signal from the Receive Pulse Comparator 808. The brief pulse is also directed to a pulse amplifier (i.e., the driver 814) where the voltage is increased before the brief pulse is sent to the transmitting transducer such as a Lead Zirconate Titanate type of piezoelectric transducer via the Output port 804. The Valid Receive Pulse Detector circuitry 700 operates as described above with respect to FIG. 7.

Figure 9:
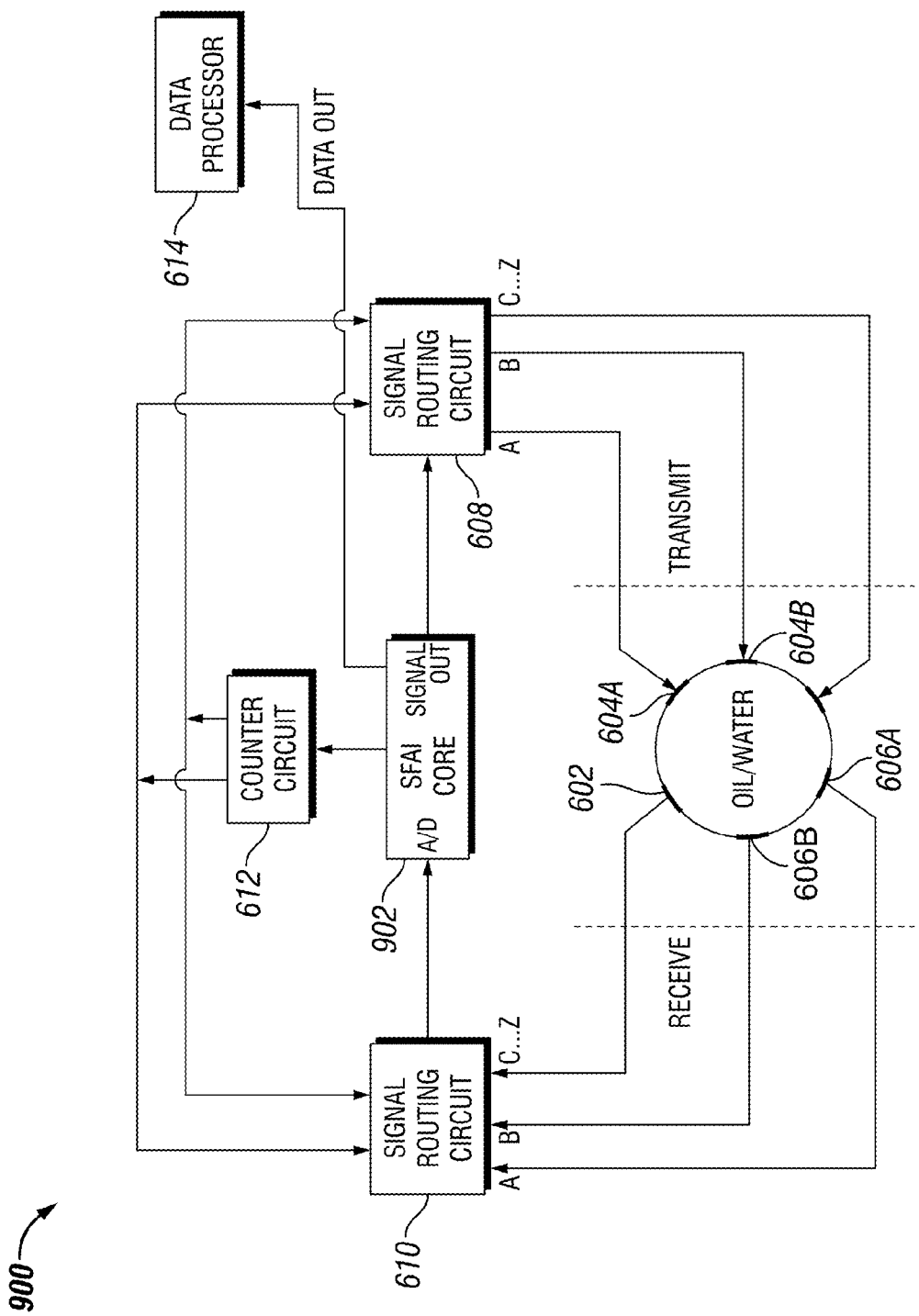
FIG. 9 illustrates a block diagram of a system for multiphase fluid flow measurement that is based on Swept Frequency Acoustic Interferometry (SFAI) and that includes multiple transducers such as shown in FIG. 4 according to another example embodiment.

FIG. 9 illustrates a block diagram of a system 900 for multiphase fluid flow measurement that is based on Swept Frequency Acoustic Interferometry (SFAI) and that includes multiple transducers such as shown in FIG. 4 according to another example embodiment. The system 900 is similar to the system 600 of FIG. 6 and generally operates in substantially the same manner as the system 600. The primary difference between the systems 600 and 900 is that the system 900 includes an SFAI core 902 instead of the sing-a-round core 607 of FIG. 6. SFAI refers to a non-invasive identification or monitoring of fluid composition using acoustic inspection techniques described in U.S. Pat. No. 5,767,407, which is incorporated herein by reference.

In some example embodiments, the SFAI core 602 includes an analog-to-digital (A/D) converter to convert an analog signal that may be received from the Signal routing circuit 610 to a digital signal for further processing by the SFAI core 902. To illustrate, the electrical signals generated by the receiving transducers 606A, 606B, . . . and sequentially transferred to the SFAI core 902 may be analog signals that need to be converted into digital signals.

In some example embodiments, the SFAI core 902 may provide an output signal Signal Out, which may be a pulse or another type of signal. To illustrate, Signal Out may be a chirp output. A chirp is a signal that has a frequency that increases ("Upchirp") or decreases ("Downchirp") with time. For purposes of present description, a chirp refers to a sweep signal, which also may be known as a quadratic phase signal. In some example embodiments, the SFAI core 902 may be able to provide multiple output signals to the data processing device 614 for a broad characterization of the fluid flowing through the pipe 602.

Figure 10:
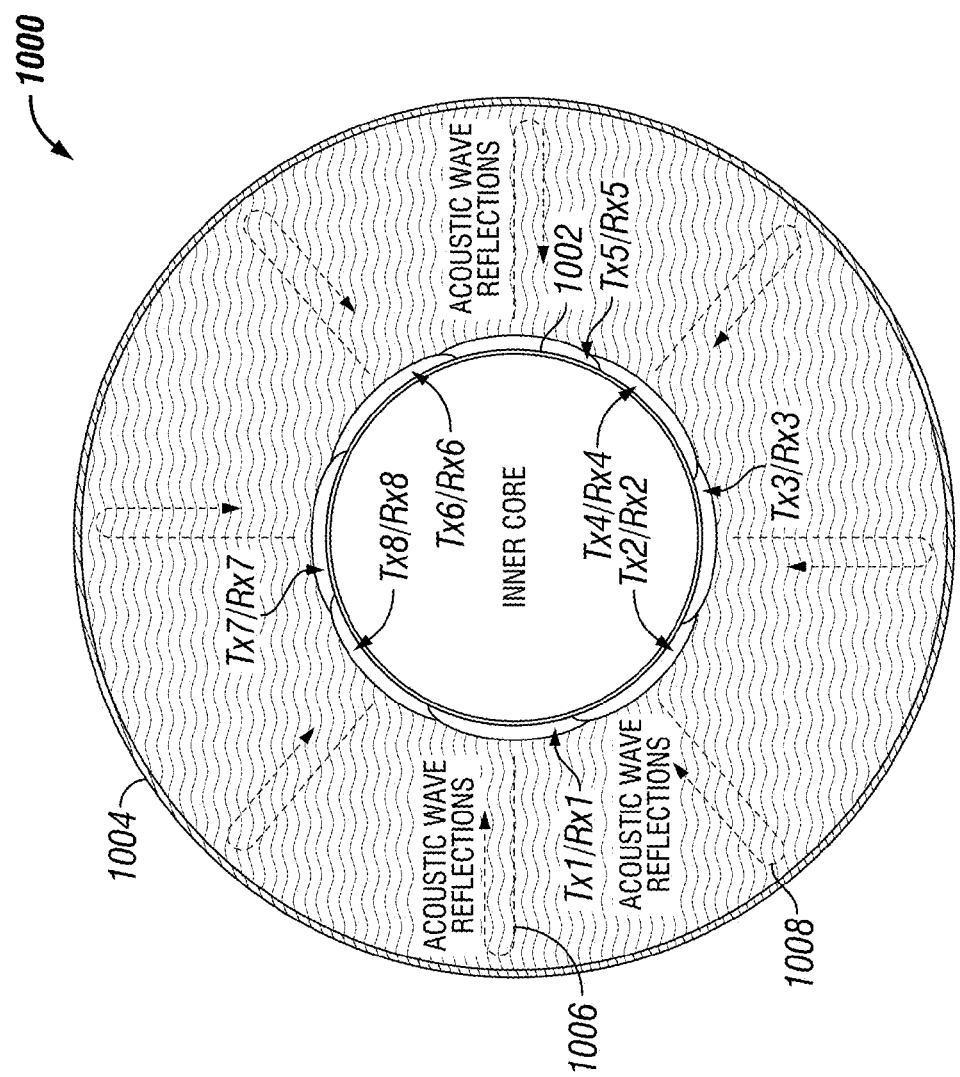
FIG. 10 illustrates a system of multiple transducers that are positioned circumferentially around an inner pipe and operate to interrogate a fluid that flows between the inner pipe and an outer pipe positioned around the inner pipe according to an example embodiment.

FIG. 10 illustrates a system 1000 of multiple transducers Tx1/Rx1-Tx8/Rx8 that are positioned circumferentially around an inner pipe 1002 and operate to interrogate a fluid that flows in the annulus between the inner pipe 1002 and an outer pipe 1004 according to an example embodiment. In some example embodiments, the transducers Tx1/Rx1-Tx8/Rx8 may generally be in a horizontal plane. In some example embodiments, the transducers Tx1/Rx1-Tx8/Rx8 are piezoelectric transducers that are configurable to switch between transmitting an acoustic signal and receiving the reflected acoustic signal. For example, the transducers Tx1/Rx1-Tx8/Rx8 may be transducers that can be configured to receive a respective electrical signal and to generate an acoustic signal in one mode, and to receive an acoustic signal and to generate an electrical signal in another mode.

As illustrated in FIG. 10, the transducers Tx1/Rx1-Tx8/Rx8 are positioned circumferentially around the wall of the inner pipe 1004. The inner pipe 1002 is positioned within the outer pipe 1004. The wall of the inner pipe 1002 and the wall of the outer pipe 1004 define an annular space between the inner pipe 1002 and the outer pipe 1004. The transducers Tx1/Rx1-Tx8/Rx8 may be exposed to the multiphase fluid flowing through the annulus. Each transducer Tx1/Rx1-Tx8/Rx8 is oriented to transmit an acoustic signal toward the outer pipe 1004 such that the acoustic signal from each transducer Tx1/Rx1-Tx8/Rx8 is reflected off the outer pipe 1004 back primarily toward the particular transducer Tx1/Rx1-Tx8/Rx8. To illustrate, the acoustic signal 1006 transmitted by the transducer Tx1/Rx1 is reflected off the outer pipe 1004 and received by the transducer Tx1/Rx1. For example, after the transducer Tx1/Rx1 transmits the acoustic signal 1006 while operating as a transmitting transducer, the transducer Tx1/Rx1 is then configured to operate as a receiving transceiver to receive the acoustic signal 1006 reflected off the outer pipe 1004. Similarly, the acoustic signal 1008 transmitted by the transducer Tx2/Rx2 is reflected off the outer pipe 1004 and received by transducer Tx2/Rx2. After the transducer Tx2/Rx2 transmits the acoustic signal 1008 while operating as a transmitting transducer, the transducer Tx2/Rx2 is then configured to operate as a receiving transceiver to receive the acoustic signal 1008 after reflection off the outer pipe 1004. The remaining transducers Tx3/Rx3-Tx8/Rx8 are also configurable to operate as transmitting and receiving transducers in a similar manner.

In some example embodiments, the acoustic signals generated by the transducer Tx1/Rx1-Tx8/Rx8 may diverge as the acoustic signals travel toward the outer pipe 1004 and may converge (due to the circular cross-section of the outer pipe 1004) toward the respective transducers after being reflected off the outer pipe 1004. Alternatively, the acoustic signals may travel toward the outer pipe 1004 and back toward the inner pipe 1002 without significant divergence or convergence depending on the shapes of the pipes 1002, 1004, which may have, for example, a polygonal instead of a circular cross-section.

In some example embodiments, each one of the transducers Tx1/Rx1-Tx8/Rx8 may include two transducers such that one of the two transducers operates as a transmitting transducer Tx and the second transducer operates as a receiving transducer Rx. For example, the transmitting transducer Tx1 may be oriented to transmit the acoustic signal 1006 toward the outer pipe 1004 such that the acoustic signal 1006 is reflected back primarily toward the receiving transducer Rx1. The other transducers Tx2/Rx2-Tx8/Rx8 may also operate in a similar manner.

In some example embodiments, the individual transducers Tx1/Rx1-Tx8/Rx8 are operated sequentially to interrogate the fluid flowing through annulus between the inner pipe 1002 and the outer pipe 1004. For example, the transducer Tx1/Rx1 may transmit the acoustic signal 1006 and receive the acoustic signal reflected off the pipe 1004 before another one of the transducers transmits an acoustic signal.

In some alternative embodiments, two or more (e.g., four) of the transducers Tx1/Rx1-Tx8/Rx8 may transmit acoustic signals and receive the reflected acoustic signals before another two or more of the transducers Tx1/Rx1-Tx8/Rx8 transmit acoustic signals and receive the reflected acoustic signals. To illustrate, the transducers Tx1/Rx1, Tx3/Rx3, Tx5/Rx5, and Tx7/Rx7 may first transmit acoustic signals toward the outer pipe 1004 substantially simultaneously and receive the respective reflected acoustic signals before Tx2/Rx2, Tx4/Rx4, Tx6/Rx6, and Tx8/Rx8 transmit acoustic signals toward the outer pipe 1004 and receive respective reflected acoustic signals. The transducers that transmit acoustic signals simultaneously may be selected such that the acoustic signals do not meaningfully interfere with each other.

The travel time of the acoustic signals from the transducer Tx1/Rx1-Tx8/Rx8 to the outer pipe 1004 and back to the transducer Tx1/Rx1-Tx8/Rx8 is dependent on a composition of a portion of the multiphase fluid traversed by the respective acoustic signal. Characteristics of the multiphase fluid flowing through the pipe 1002 may be determined based on the travel times of the acoustic signals transmitted and received by the transducer Tx1/Rx1-Tx8/Rx8 through the multiphase fluid. For example, for a particular temperature of the multiphase fluid, the speed of sound through the multiphase fluid flowing through the annulus may be determined based on the distance traveled an acoustic signal and the time of travel. The speed of sound through the multiphase fluid may be correlated to known data to determine the characteristics of the fluid. By using multiple transducers, a more complete interrogation of the multiphase fluid flowing through the annulus of FIG. 10 is performed. Because of the sequential operation of the multiple transducer even when operated as groups, interference among acoustic signals transmitted by the multiple transmitting transducers is kept low.

Although the pipes 1002, 1004 are cylindrical as shown in FIG. 10, in alternative embodiments, the pipes 1002, 1004 may be polygonal. For example, the pipes 1002, 1004 may have a rectangular or hexagonal cross-section. Although a particular arrangement of the transducers Tx1/Rx1-Tx8/Rx8 is shown in FIG. 10, in alternative embodiments, the transducers Tx1/Rx1-Tx8/Rx8 may be arranged in a different configuration without departing from the scope of this disclosure. Further, although eight transducers are shown in FIG. 10, in alternative embodiments, fewer or more than eight transducers may be used.

Figure 11:
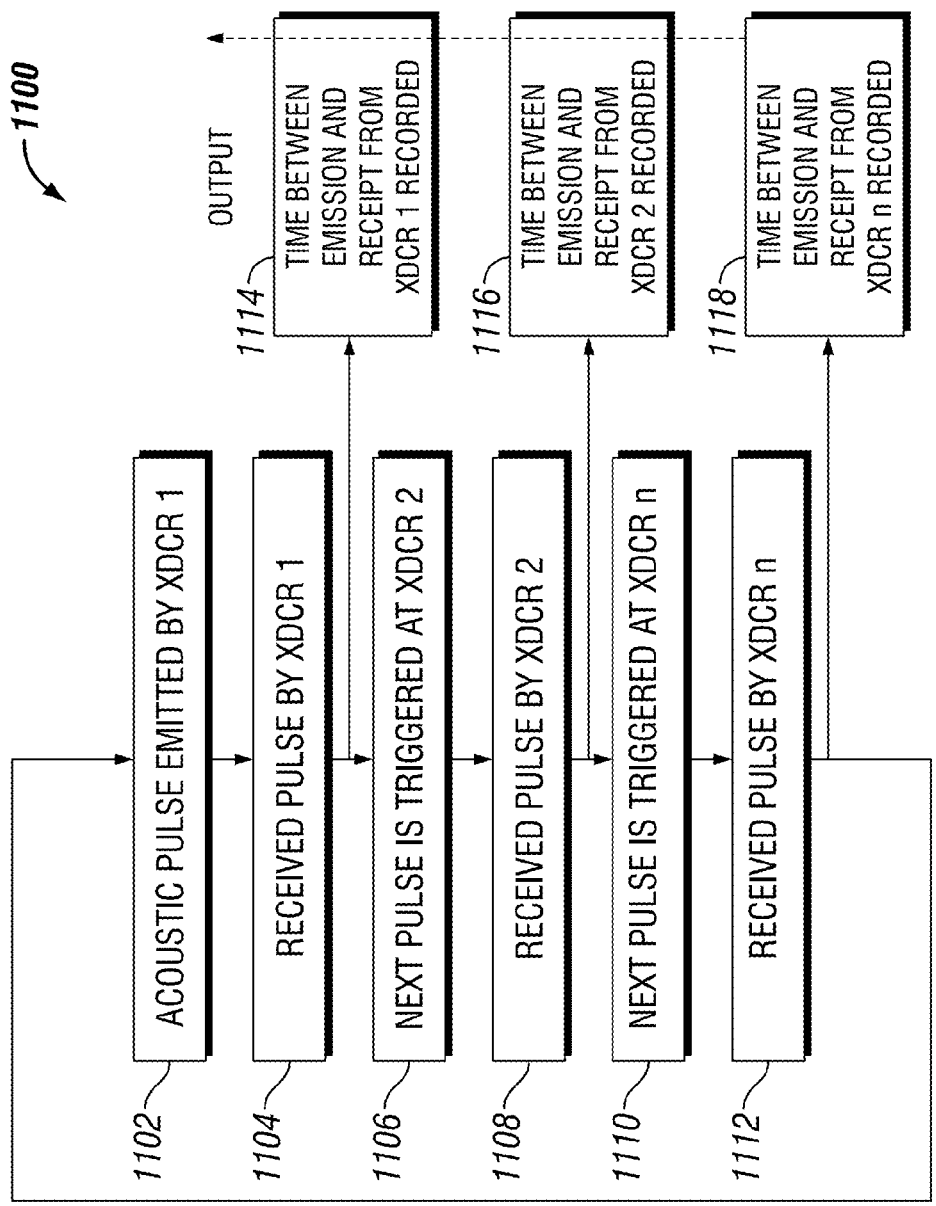
FIG. 11 illustrates a sequence of operation of the multiple transducers such as the transducers of FIG. 10 according to an example embodiment.

FIG. 11 illustrates a sequence of operation of multiple transducers such as the transducers of FIG. 10 according to an example embodiment. Referring to FIGS. 10 and 11, transducer XDCR 1 emits/transmits an acoustic pulse at step 1102. At step 1104, the acoustic signal transmitted by the transducer XDCR 1 and reflected off the outer pipe 1004 is received by the transducer XDCR 1. For example, the transducer XDCR 1 may be the transducer Tx1/Rx1 of FIG. 10. At step 1114, the time between the transmission and the reception by the transducer XDCR 1 is recorded or otherwise processed.

At step 1106, the next acoustic pulse is triggered/transmitted by a transducer XCDR 2. For example, step 1106 may be performed without the completion of step 1114. The reflection of the acoustic pulse transmitted by the transducer XCDR 2 off the outer pipe 1004 is received by the transducer XCDR 2. At step 1116, the time between the transmission and the reception by the transducer XDCR 2 is recorded and/or otherwise processed. Other transducers may operate sequentially in a similar manner until the last transducer XCDR n (where n is an integer greater than 2) transmits an acoustic signal at step 1110 and receives the reflected acoustic signal at step 1112. At step 1118, the time between the transmission and the reception by the transducer XDCR n is recorded or otherwise processed. The time between transmission and reception by other transducers between XCDR 2 and XCDR n are also recorded in a similar manner.

In some example embodiments, the times recorded and/or processed at steps 1114, 1116, 1118 may be provided as output for further processing. For example, Fast Fourier Transform and other methods may be implemented on the data conveying the recorded or processed time information.

Although the sequence of operation described with respect to FIG. 11 is based on operations of transducers XDCR 1-XDCR n, in alternative embodiments, two or more transducers may be operated substantially simultaneously at each of the transmitting and receiving steps described above. For example, by selecting transducers that are unlikely to result in interference among simultaneously transmitted acoustic signals (e.g., transducers Tx1/Rx1 and Tx5/Rx5 shown in FIG. 10) to simultaneously transmit the acoustic signals, efficient and reliable interrogation of the fluid in the annulus may be performed.

Figure 12:
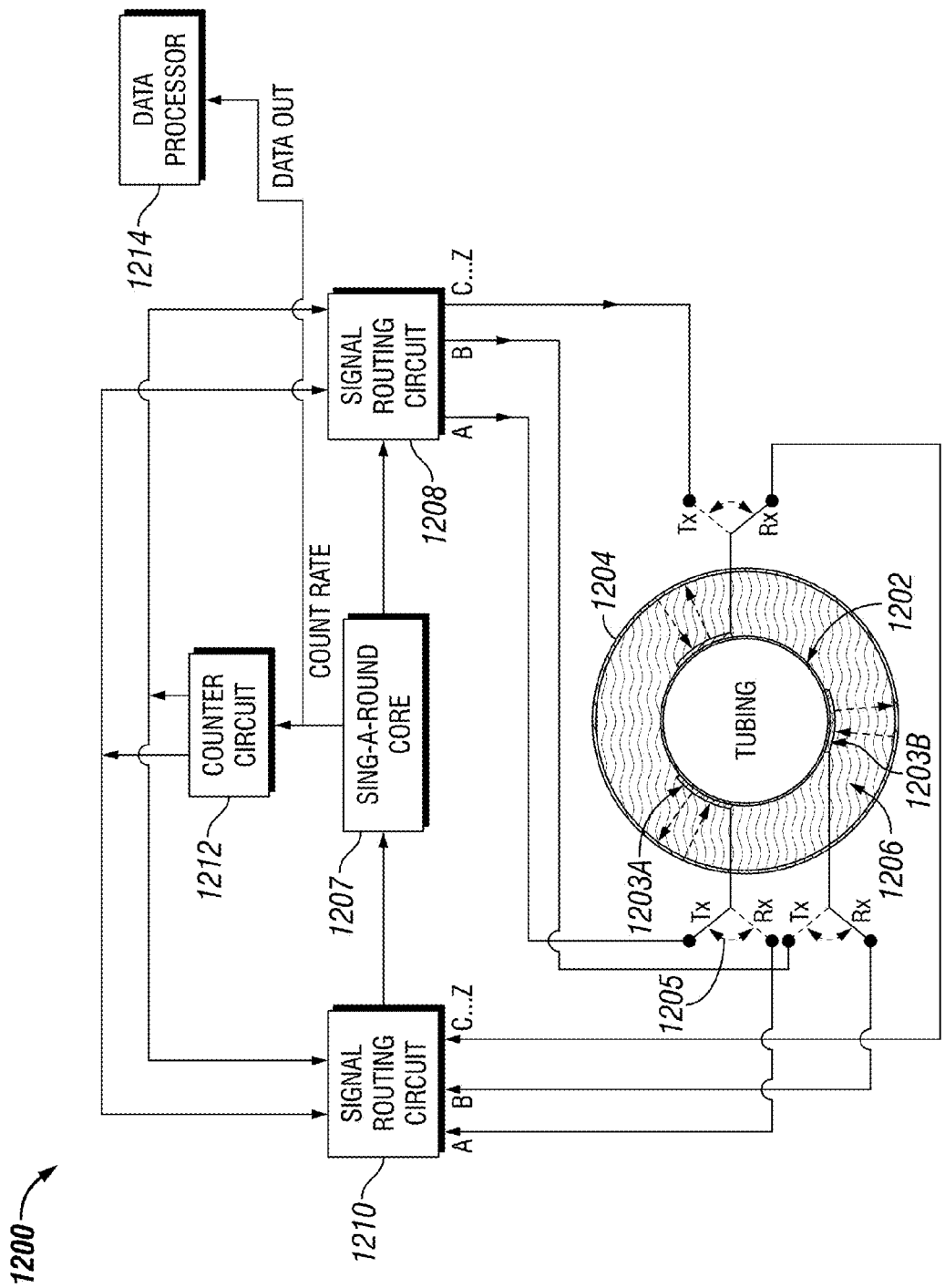
FIG. 12 illustrates a block diagram of a system for multiphase fluid flow measurement that includes multiple transducers such as shown in FIG. 10 according to an example embodiment.

FIG. 12 illustrates a block diagram of a system 1200 for multiphase fluid flow measurement that includes multiple transducers such as shown in FIG. 10 according to an example embodiment. In some example embodiments, the system 1200 may be used to implement the operations shown in and described with respect to FIG. 11.

As shown in FIG. 12, the system includes an inner pipe 1202, which may be the same or similar to the inner pipe 1002 of FIG. 10. In some example embodiments, the system 1200 includes a sing-a-round core 1207 that controls some operations of the system 1200. For example, the sing-a-round core 1207 may be a signal processing device. The system 1200 also includes a signal routing circuit 1208, a signal routing circuit 1210, and a counter 1212. In general, the sing-a-round core 1207, the signal routing circuit 1208, the signal routing circuit 1210, and the counter 1212 operate in substantially the same manner as described with respect to the sing-a-round core 607, the signal routing circuit 608, the signal routing circuit 610, and the counter 612 of FIG. 6. Multiple transducers 1203A, 1203B, . . . are circumferentially attached to the inner pipe 1202. For example, each of the transducers 1203A, 1203B, . . . are positioned and oriented to transmit a respective acoustic signal toward the outer pipe 1204, which may be the same or similar to the outer pipe 1004 of FIG. 10.

In some example embodiments, the transducers 1203A, 1203B, . . . may switch between operating as a transmitting transducer and a receiving transducer based on a setting of a respective switch such as the switch 1205. For example, the switch 1205 may be controlled by the sing-a-round core 1207 or another component of the system.

Electrical signals are provided to the transducers 1203A, 1203B, . . . from the sing-a-round core 1208 sequentially through the signal routing circuit 1208 in a similar manner described with respect to the system 600 of FIG. 6. The acoustic signals transmitted by the transducers 1203A, 1203B, . . . through the multiphase fluid in the annulus 1206 and received by the transducers 1203A, 1203B, . . . after reflection off the outer pipe 1204 are provided to the sing-a-round core 1207 via the signal routing circuit 1210 in a similar manner described with respect to the system 600 of FIG. 6.

In some example embodiments, electrical signal other than electrical pulses may be provided to the transducers 1203A, 1203B, . . . to generate acoustic signals. Further, the electrical signals provided by the sing-a-round core 1207 to the different transmitting transducers 1203A, 1203B, . . . via the decoder input selector 1208 may have different characteristics (e.g., different amplitudes, pulse width, etc.) from each other. Accordingly, the acoustic signals transmitted by the different transducers 1203A, 1203B, . . . may have different characteristics that may be used in characterizing the fluid flowing through the annulus 1206.

Figure 13:
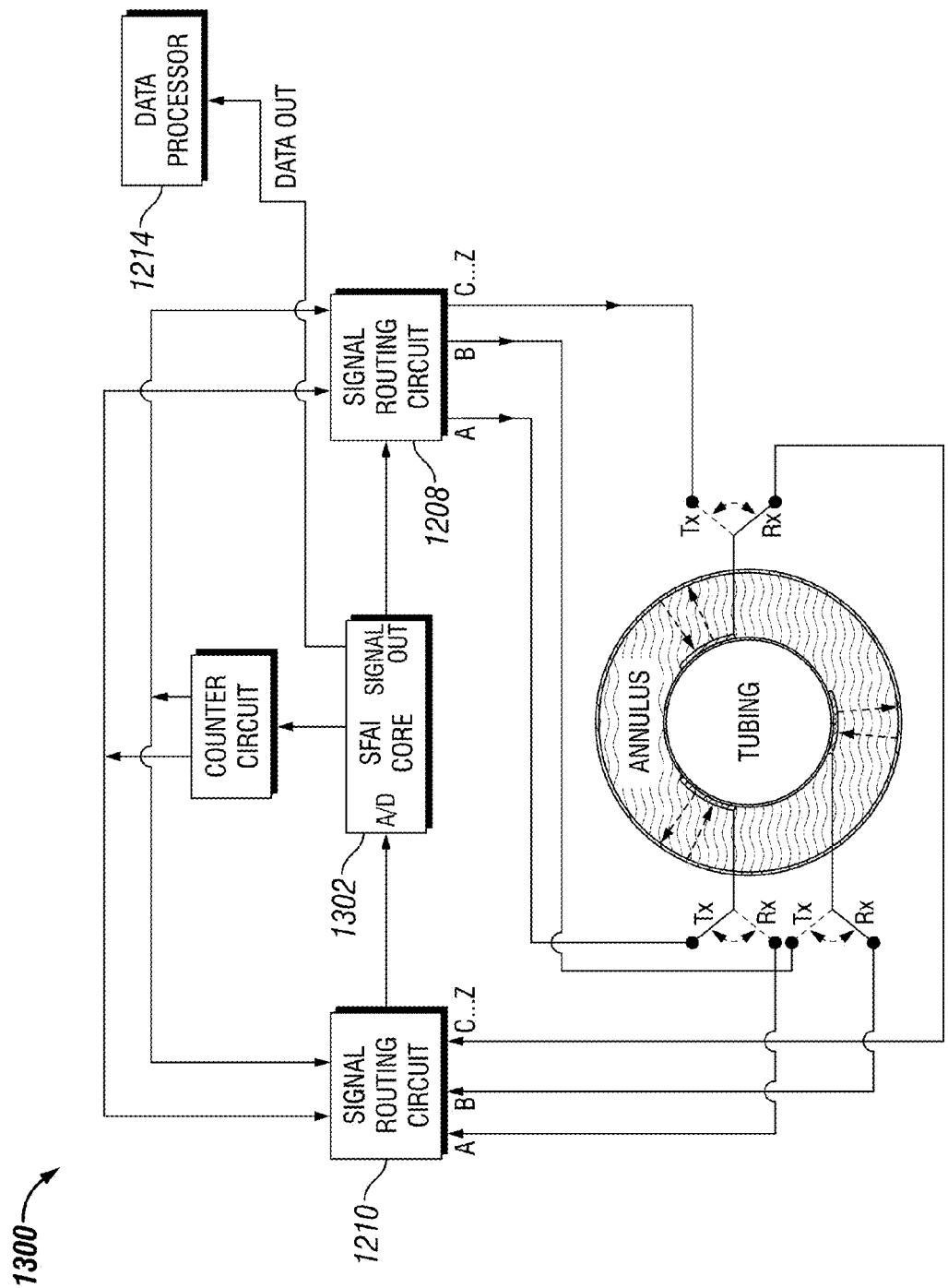
FIG. 13 illustrates a block diagram of a system for multiphase fluid flow measurement that is based on an SFAI core and that includes multiple transducers such as shown in FIG. 10 according to another example embodiment.

FIG. 13 illustrates a block diagram of a system 1300 for multiphase fluid flow measurement that is based on SFAI and that includes multiple transducers such as shown in FIG. 10 according to another example embodiment. The system 1300 is similar to the system 1200 of FIG. 12 and generally operates in substantially the same manner as the system 1200. The primary difference between the systems 1200 and 1300 is that the system 1300 includes an SFAI core 1302 instead of the sing-a-round core 1207 of FIG. 12. As described with respect to FIG. 9, SFAI refers to a non-invasive identification or monitoring of fluid composition using acoustic inspection techniques described in U.S. Pat. No. 5,767,407, which is incorporated herein by reference. The SFAI core 1302 operates in the similar manner described with respect to FIG. 9.

Figure 14A:
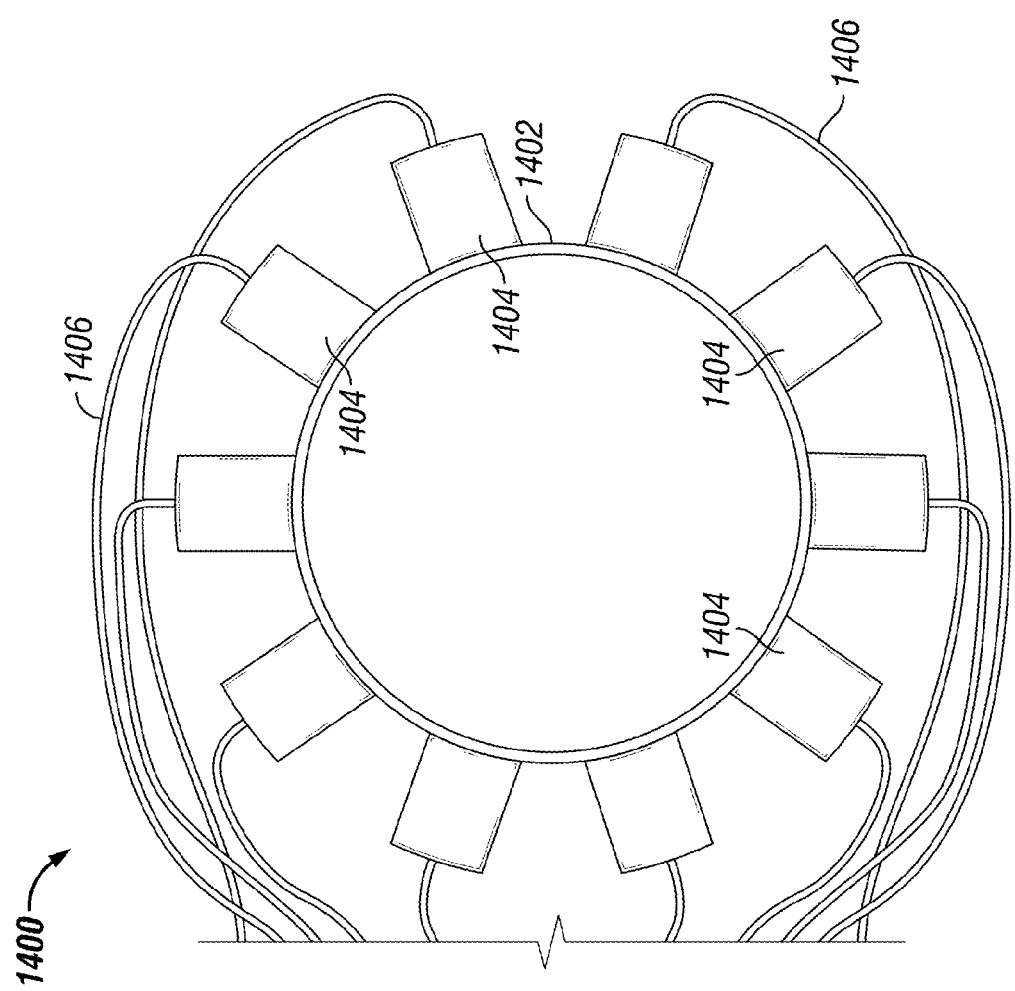
FIGS. 14A and 14B illustrate different views of a prototype system for multiphase fluid flow measurement according an example embodiment.
Figure 14B:
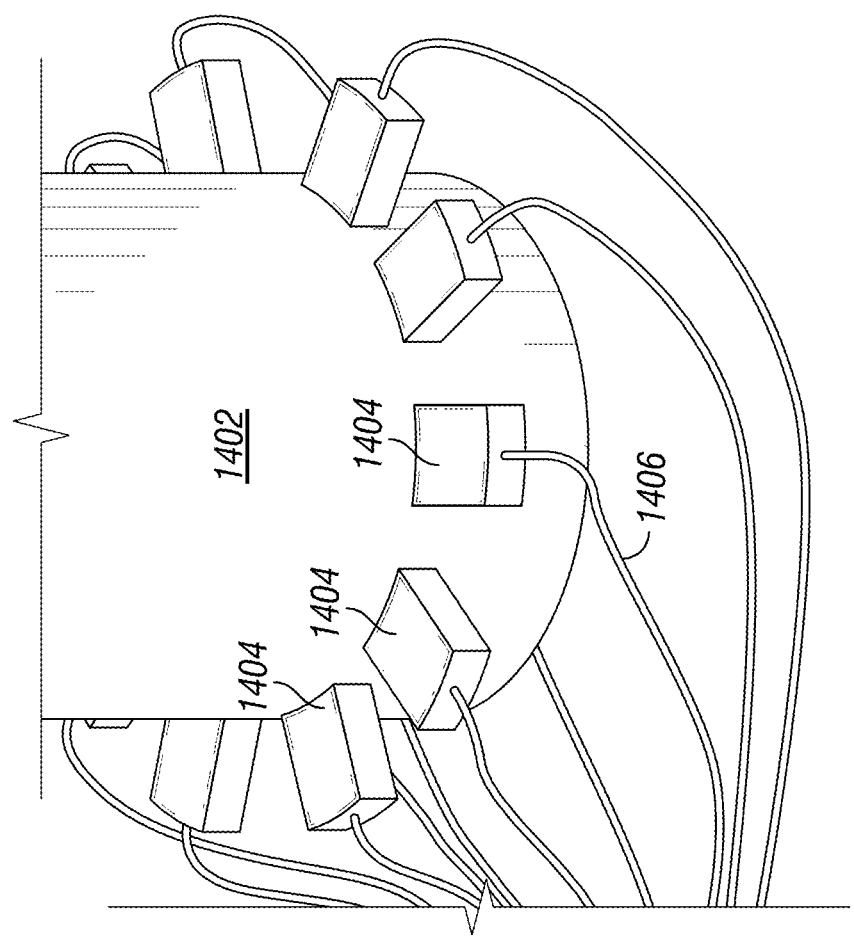

FIGS. 14A and 14B illustrate different views of a prototype system 1400 for multiphase fluid flow measurement according an example embodiment. In FIG. 14A, a top view of the system 1400 is shown. In FIG. 14B, a side view of the system 1400 is shown. In FIGS. 14A and 14B, multiple transducers 1404 are circumferentially attached to the pipe 1402, and wires 1406 extend from the transducers 1404 to a device such the signal routing circuit 610 or the signal routing circuit 608 shown in FIG. 6. The transducers 1404 are disposed on the outside surface of the pipe 1402 and are not exposed to the fluid within the pipe 1402. In some example embodiments, the transducers 1404 correspond to the transducers described with respect to FIGS. 6-9.

Figure 15:
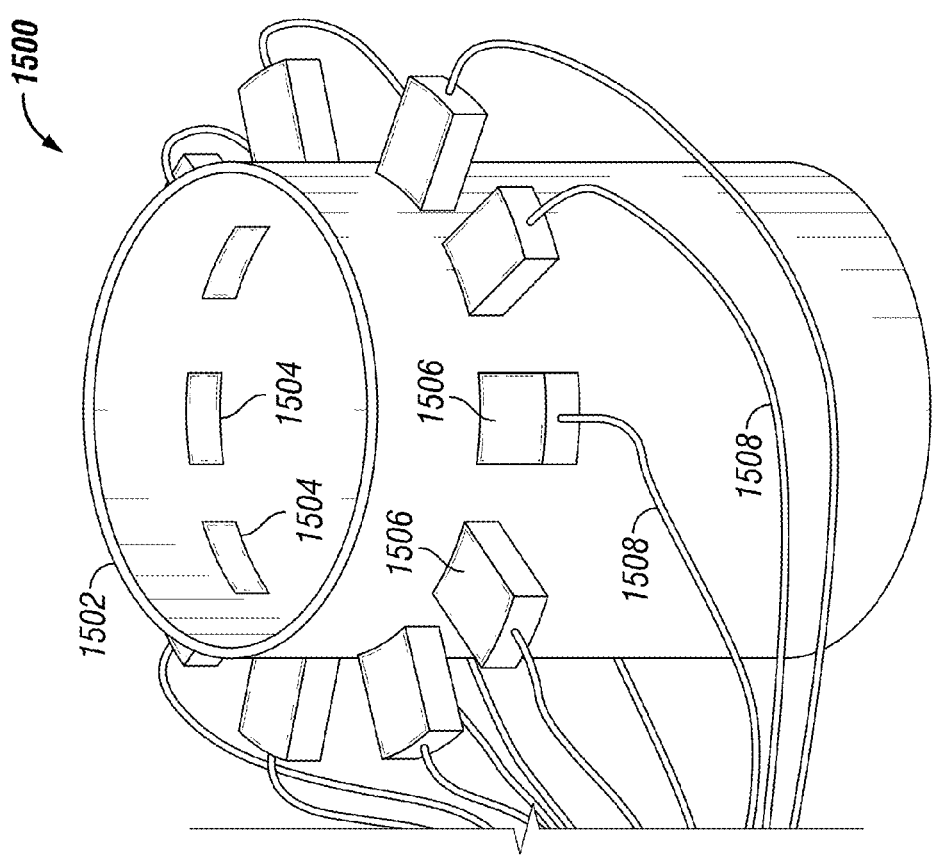
FIG. 15 illustrate a prototype system for multiphase fluid flow measurement according another example embodiment.

FIG. 15 illustrates a prototype system 1500 for multiphase fluid flow measurement according another example embodiment. The prototype system 1500 includes a pipe (conduit) 1502. The pipe 1502 includes openings 1504 providing access from outside of the pipe 1502 to a multiphase fluid that may flow through the pipe 1502. The system 1502 also includes transducers 1506 that are circumferentially disposed around the outside surface of the pipe 1502 such that a portion of each transducer 1506 is disposed at a respective one of the openings 1504. By being disposed at the openings 1504, the transducers 1506 are exposed to the fluid flowing through the pipe 1502 to more effectively transmit and receive acoustic signal to and from the fluid. The wires 1508 may be used to carry electrical signals to and from the transducers 1506 in a manner described above.

Figure 16A:
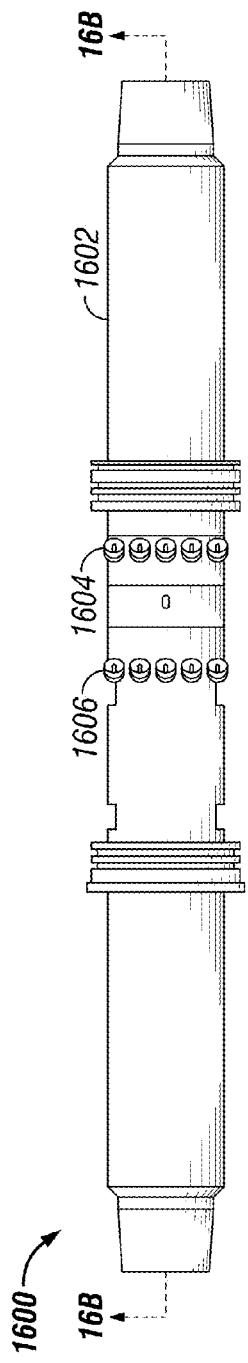
FIGS. 16A-16C illustrate a multi-transducer system for estimating flow characteristics of a fluid flowing through a pipe according to an example embodiment.
Figure 16B:
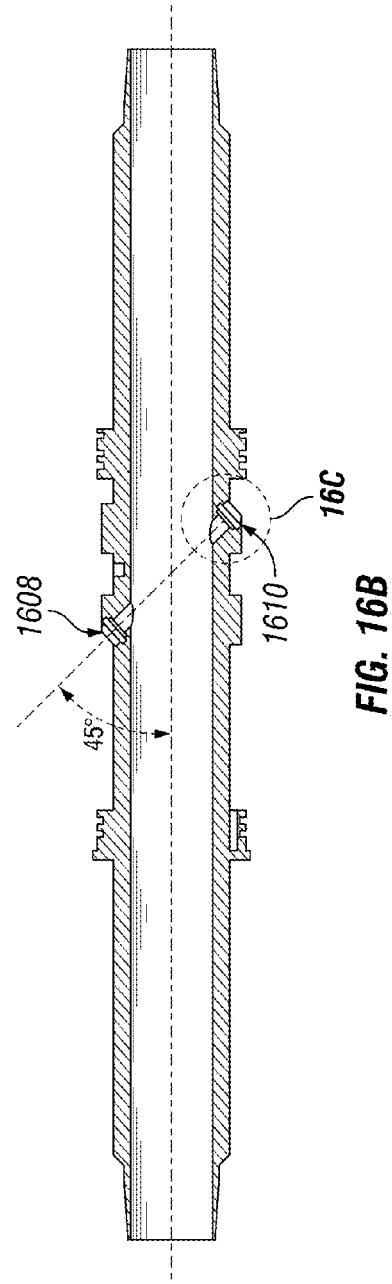
Figure 16C:
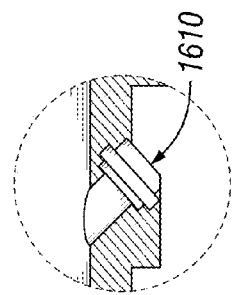

FIGS. 16A-16C illustrate a multi-transducer system 600 for estimating flow characteristics of a fluid flowing through a pipe 1602 according to an example embodiment. As illustrated in FIG. 16A, a first set of transducers 1604 and a second set of transducers 1606 (e.g., piezoelectric transducers) that are disposed around a pipe 1602. Both sets of transducers 1604, 1606 are configurable to operate as transmitting transducers and receiving transducers. For example, the first set of transducers 1604 may transmit acoustic (e.g., ultrasonic) signals toward the second set of transducers 1606 that are operating as receiving transducers. After the travel time of transmitted acoustic signals from the first set of transducers 1604 to the second set of transducers 1606 through the fluid is recorded and/or otherwise processed, the second set of transducers 1606 transmit acoustic (e.g., ultrasonic) signals toward the first set of transducers 1604 that are now operating as receiving transducers. The travel time of transmitted acoustic signals from the second set of transducers 1606 to the first set of transducers 1604 through the fluid is similarly recorded and/or otherwise processed. The travel times of the acoustic signals in both directions are evaluated, for example, based on the difference in the travel times to estimate the flow characteristics of the fluid flowing through the pipe 1602.

As shown in FIGS. 16B and 16C, the individual respective transducers of the two sets of transducers 1604, 1606 may be oriented at a non-zero angle relative to the flow direction of the fluid. For example, the transducers 1608 and 1610 are oriented at approximately 45 degrees relative to the flow direction of the fluid through the pipe to determine the fluid velocity by differential time of flight measurement. Flow rate can be determined by either recording the time it take transducers 1606 to match a reading from transducers 1604, or by measuring the difference in time of flight from transducer 1608 to transducer 1610 and from the transducer 1608 to the transducer 1610.

Although some embodiments have been described herein in detail, the descriptions are by way of example. The features of the embodiments described herein are representative and, in alternative embodiments, certain features, elements, and/or steps may be added or omitted. Additionally, modifications to aspects of the embodiments described herein may be made by those skilled in the art without departing from the spirit and scope of the following claims, the scope of which are to be accorded the broadest interpretation so as to encompass modifications and equivalent structures.

The invention claimed is:

1. A system for determining characteristics of a multiphase fluid, the system comprising:
    a pipe; and
    multiple pairs of transducers positioned circumferentially around the pipe, wherein each pair of transducers includes a transmitting transducer and a receiving transducer, wherein the transmitting transducer of each pair of transducers is oriented to transmit a respective acoustic signal toward the receiving transducer of the pair of transducers, wherein the transmitting transducer of each pair of transducers is operable to transmit the respective acoustic signal sequentially with respect to other transmitting transducers of the multiple pairs of transducers, and wherein a reception of a first acoustic signal transmitted by a transmitting transducer of a first pair transducers of the multiple pairs of transducers is completed by a receiving transducer of the first pair transducers before a transmitting transducer of another pair of transducers of the multiple pairs of transducers transmits a second acoustic signal.

2. The system of claim 1, further comprising a multiphase fluid flowing through the pipe, wherein a travel time of an acoustic signal from a transmitting transducer of a pair of transducers to a receiving transducer of the corresponding pair of transducers is dependent on a composition of a portion of the multiphase fluid traversed by the acoustic signal.

3. The system of claim 1, further comprising a signal processing device to control sequential generation of the acoustic signals by the transmitting transducers of the multiple pairs of transducers.

4. The system of claim 3, wherein the transmitting transducer of each pair of transducers generates the respective acoustic signal based on an electrical signal provided to the transmitting transducer.

5. The system of claim 4, wherein the electrical signal includes an electrical pulse.

6. The system of claim 3, wherein the signal processing device is configured to:
    receive electrical signals from the receiving transducers of the multiple pairs of transducers;
    to generate an output electrical signal indicative of travel times of the acoustic signals through the multiphase fluid.

7. The system of claim 6, further comprising a data processing device configured to receive the output electrical signal and to determine characteristics of the multiphase fluid.

8. The system of claim 1, wherein a wall of the pipe has a plurality of openings, wherein each transducer of the multiple pairs of transducers is positioned at a respective opening of the plurality of openings to be exposed to a multiphase fluid in the pipe through the respective opening of the plurality of openings.

9. The system of claim 1, wherein flow characteristics of a multiphase fluid flowing through a pipe are estimated based on the travel times of acoustic signals transmitted by transmitting transducers of the multiple pairs of transducers and received by receiving transducers of the multiple pairs of transducers.

10. A system for measuring characteristics of a multiphase fluid, the system comprising:
    an inner pipe;
    an outer pipe, wherein the inner pipe is positioned within the outer pipe, the inner pipe and the outer pipe defining an annular space; and
    a plurality of transducers positioned circumferentially around the inner pipe, wherein each transducer is configurable to operate as a transmitting transducer and a receiving transducer, wherein each transducer is oriented to transmit an acoustic signal toward the outer pipe such that the acoustic signal is reflected off the outer pipe toward the transducer for reception by the transducer.

11. The system of claim 10, further comprising a multiphase fluid within the annular space, wherein a travel time of the acoustic signal from each transducer to the outer pipe and back to the transducer is dependent on a composition of a portion of the multiphase fluid traversed by the respective acoustic signal, and wherein characteristics of the multiphase fluid are determined based on the travel time of the acoustic signal transmitted by each transducer.

12. The system of claim 11, further comprising a signal processing device to control sequential transmissions of acoustic signals by the transducers, wherein a first transducer of the plurality of transducers transmits a first acoustic signal and receives the first acoustic signal reflected off the outer pipe before another acoustic signal is transmitted by remaining one or more transducers of the plurality of transducers.

13. The system of claim 11, wherein two or more transducers of the plurality of transducers transmit acoustic signals substantially simultaneously.

14. The system of claim 10, wherein each transducer generates an output electrical signal based on the acoustic signal transmitted by the transducer and received by the transducer after being reflected off the outer pipe and wherein the output electrical signal is provided to a signal processing device.

15. The system of claim 14, wherein each transducer generates an acoustic signal based on an electrical signal generated by the signal processing device and provided to the transducer.

16. A method for determining characteristics of a multiphase fluid, the system comprising:
- transmitting a first acoustic signal by a first transmitting transducer;
- receiving the first acoustic signal by a first receiving transducer;
- transmitting a second acoustic signal by a second transmitting transducer after receiving the first acoustic signal by the first receiving transducer;
- receiving the second acoustic signal by a second receiving transducer;
- determining a travel time of the first acoustic signal through a first portion of a multiphase fluid; and
- determining a travel time of the second acoustic signal through a second portion of the multiphase fluid, wherein the first transmitting transducer, the first receiving transducer, the second transmitting transducer, and the second receiving transducer are positioned circumferentially around the pipe.

17. The method of claim 16, wherein the first transmitting transducer and the first receiving transducer are positioned diametrically opposite each other, wherein the second transmitting transducer and the second receiving transducer are positioned diametrically opposite each other, and wherein the multiphase fluid flows through the pipe.

18. The method of claim 16, wherein the pipe is positioned within an outer pipe, wherein the multiphase fluid flows in an annular space between a wall of the inner pipe and a wall of the outer pipe, and wherein the first transmitting transducer and the first receiving transducer are the same transducer operable to transmit the first acoustic signal and to receive the first acoustic signal reflected of the wall of the outer pipe.

19. The method of claim 16, further comprising:
- providing a first electrical signal to the first transmitting transducer such that the first transmitting transducer generates the first acoustic signal; and
- receiving a second electrical signal from the first receiving transducer, wherein the second electrical signal is generated by the first receiving transducer based on the first acoustic signal.

20. The method of claim 19, further comprising:
- determining characteristics of the multiphase phase fluid based on a travel time of the first acoustic signal through a first portion of the multiphase fluid and based on a travel time of a second acoustic signal through a second portion of the multiphase fluid.

* * * * *